United States Patent
Boyd et al.

[11] Patent Number: 5,360,582
[45] Date of Patent: Nov. 1, 1994

[54] NONLINEAR OPTICAL MATERIALS CONTAINING POLAR DISULFONE-FUNCTIONALIZED MOLECULES

[75] Inventors: Gary T. Boyd, Woodbury; George V. Tiers, St. Paul; Cecil V. Francis, Woodbury; Eugene P. Janulis, Mahtomedi, all of Minn.; Robert J. Koshar, Sun City West, Ariz.; Louis M. Leichter, Mendota Heights, Minn.

[73] Assignee: Minnesota Mining and Manufacturing Company, St. Paul, Minn.

[21] Appl. No.: 730,225

[22] Filed: Jul. 15, 1991

[51] Int. Cl.$^5$ .............................. F21V 9/00
[52] U.S. Cl. ........................ 252/582; 252/587; 359/328
[58] Field of Search ............ 252/582, 587, 589, 600; 359/328

[56] References Cited

U.S. PATENT DOCUMENTS

| | | | |
|---|---|---|---|
| 3,932,526 | 1/1976 | Koshar | 260/607 A |
| 3,933,914 | 1/1976 | Coles et al. | 260/577 |
| 3,984,357 | 11/1976 | Koshar | 260/2 R |
| 4,018,810 | 4/1977 | Skoog | 260/465 D |
| 4,069,233 | 11/1978 | Koshar | 260/347.2 |
| 4,156,696 | 5/1979 | Koshar | 260/592 |
| 4,357,405 | 11/1982 | Leichter et al. | 430/58 |
| 4,707,303 | 11/1987 | Buckley et al. | 252/583 |
| 4,859,876 | 8/1989 | Dirk et al. | 252/582 |
| 4,973,429 | 11/1990 | Decher et al. | 252/587 |
| 5,006,729 | 4/1991 | Meijer et al. | 307/425 |
| 5,041,509 | 8/1991 | Lee et al. | 252/582 |
| 5,112,532 | 5/1992 | Ninomiya et al. | 252/582 |

FOREIGN PATENT DOCUMENTS 0218938 4/1987 European Pat. Off. .
0396172A1 11/1990 European Pat. Off. .... C08F 220/34

OTHER PUBLICATIONS

R. Dagani, "Chemists Crucial to Progress in Nonlinear Optical Materials", Chem & Eng News 21–25 (Jun. 11, 1990).
E. S. Tripathy et al., "Nonlinear Optics and Organic Materials", Chemtech 747–752 (Dec. 1989).
D. S. Chem and J. Zyss "Nonlinear Optical Properties of Organic Molecules and Crystals", vols. I & II, Ch. II-7 and II-8 Academic Press, NY (1987).
I. I. Malentina et al., Inst. Org. Chem., Acad. Sci. Ukrainian SSR, Plenum Publishing (1980) (translated from Zhurnal Organicheskoi Khimii, v. 15, No. 11, pp. 2416–2417 (Nov. 1979).

*Primary Examiner*—Philip Tucker
*Attorney, Agent, or Firm*—Gary L. Griswold; Walter N. Kirn; Karl G. Hanson

[57] ABSTRACT

Nonlinear optical (NLO) compositions are disclosed which contain polar disulfone-functionalized molecules (PDFMs) incorporated in a polymeric material. When aligned noncentrosymmetrically in the polymeric material, the PDFMs generate a second-order NLO response. There is also disclosed: a method of preparing a NLO composition; novel PDFMs and novel polymers; and a new process for preparing PDFMs.

7 Claims, 1 Drawing Sheet

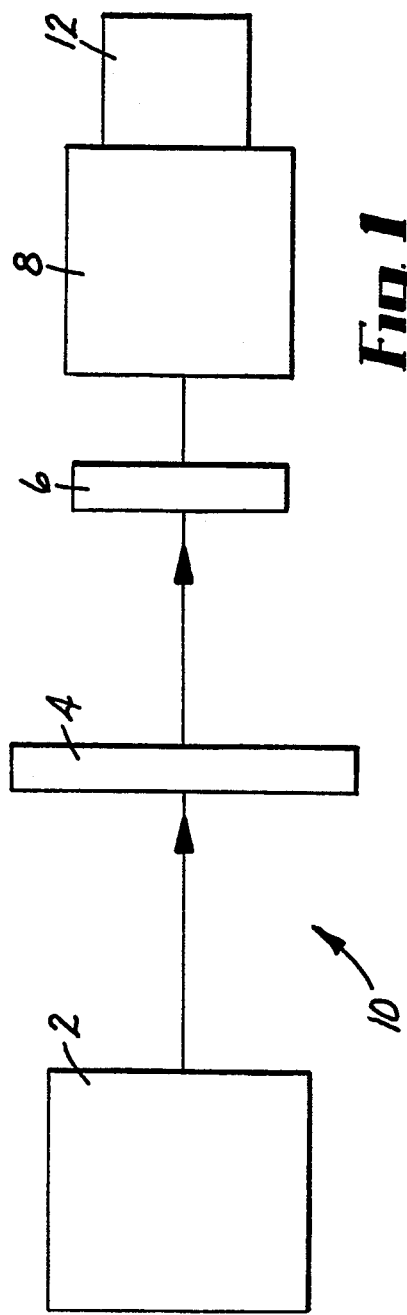
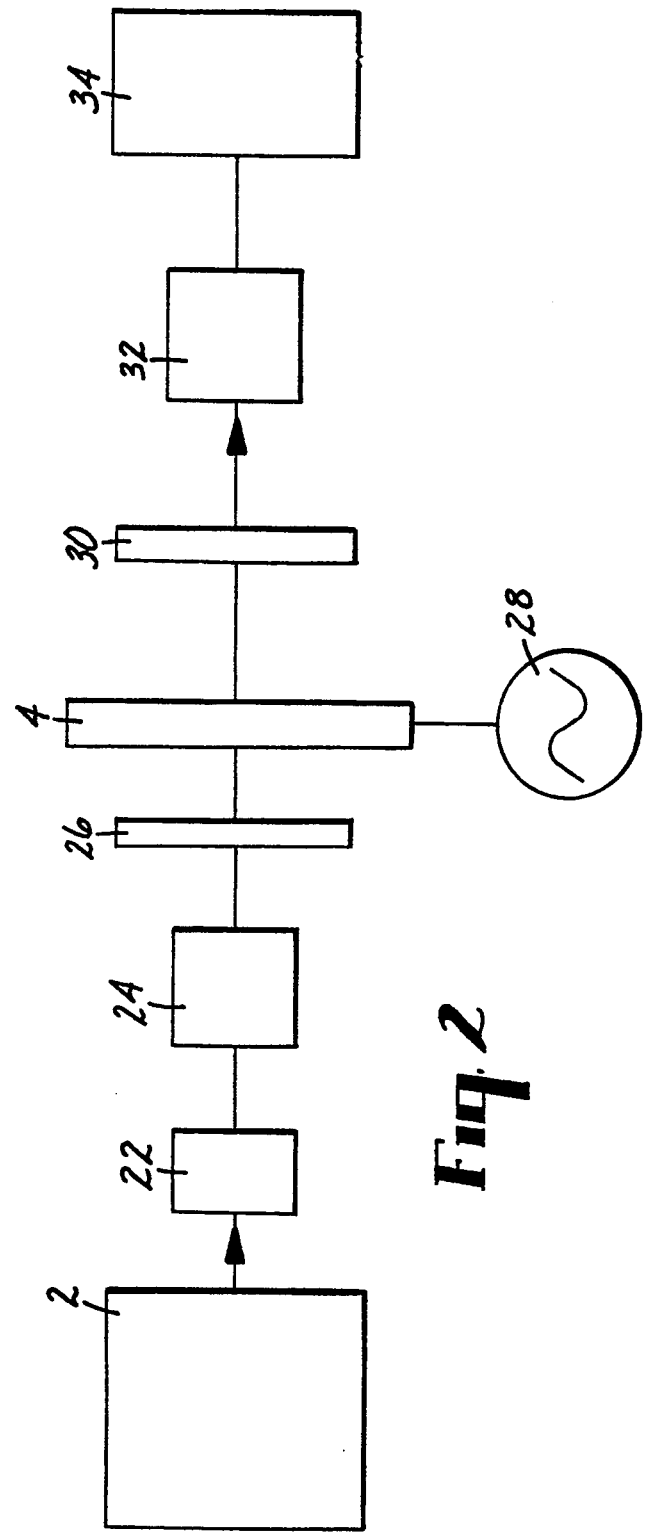

NONLINEAR OPTICAL MATERIALS CONTAINING POLAR DISULFONE-FUNCTIONALIZED MOLECULES

FIELD OF THE INVENTION

This invention pertains to (i) a nonlinear-optical (NLO) composition that contains a polymeric composition having polar disulfone-functionalized molecules (PDFMs) incorporated therein, (ii) a process for preparing a nonlinear-optical composition, (iii) a method of generating a NLO response, (iv) novel PDFMs, (v) novel polymers, and (vi) a new method of preparing PDFMs.

BACKGROUND OF THE INVENTION

Organic NLO compositions have been developed to influence the direction, frequency, amplitude, and phase of light. Typical organic NLO compositions contain a polymeric composition having polar NLO molecules incorporated therein. Typical polar NLO molecules have electron donor and acceptor groups linked by conjugated $\pi$-electron systems. When light is passed through the NLO compositions, the incorporated polar molecules generate a NLO response. Polar NLO molecules have been incorporated into polymeric compositions using one of two distinct methods.

In a first method, the polar NLO molecules are dissolved in a polymeric composition. The polar NLO molecules are referred to as "guests", and the polymeric composition is referred to as a "host". In such "guest-host" compositions, the NLO guest molecules are dispersed in the polymeric host without being bonded thereto to form a polymeric NLO composition. Guest-host polymeric NLO compositions are disclosed, for example, in EP-A-0,218,938 and U.S. Pat. No. 4,707,303.

In a second method, the polar NLO molecules are incorporated into a polymeric composition by covalently attaching the former to a polymer. An example of a polymer having NLO groups covalently bonded thereto is disclosed in U.S. Pat. No. 5,006,729.

Whether polar NLO molecules are incorporated into a polymeric composition by dispersing or bonding, the molecules need to be aligned to achieve a NLO response. It is known that NLO compositions can display a second-order response when the $\chi^{(2)}$ (chi squared) optically-responsive molecules are aligned noncentrosymmetrically. Noncentrosymmetric means that inversion symmetry is not present in the composition. Noncentrosymmetric molecular alignment has been accomplished by heating the polymeric composition to its glass transition temperature ($T_g$), applying a DC electric field across the polymeric composition to cause the incorporated NLO molecules to line up in the direction of the applied field (referred to as "poling"), and cooling the polymeric composition below $T_g$ while the electric field is still being applied.

The following publications provide general background information on NLO materials: R. Dagani, "Chemists Crucial to Progress in Nonlinear Optical Materials", Chem. & Eng News 21–25 (Jun. 11, 1990); S. Tripathy et al., "Nonlinear Optics and Organic Materials", Chemtech 747–752 (December 1989); and D. S. Chemla and J. Zyss, "Nonlinear Optical Properties of Organic Molecules and Crystals", vols. I & II,, ch II-7 and II-8 Academic Press, N.Y. (1987).

U.S. Pat. Nos. 3,932,526, 3,933,914, 3,984,357, 4,018,810, 4,069,233, 4,156,696, and 4,357,405 disclose PDFMs and processes for preparing those PDFMs. The PDFMs are disclosed to be useful as catalysts, dyes, and sensitizers. These patents do not teach or suggest that PDFMs will provide second-order NLO effects when aligned noncentrosymmetrically in a polymeric composition.

I. I. Malentina et al., Inst. Org. Chem., Acad. Sci. Ukrainian SSR, Plenum Publishing (1980) (translated from Zhurnal Organicheskoi Khimii, v. 15, n. 11, pp. 2416–17 (November 1979)) discloses preparing a disulfonyl fluoride, p-$(CH_3)_2NC_6H_4CH\!=\!C(SO_2F)_2$, from methane disulfonyl fluoride and 4-dimethylaminobenzaldehyde. No utility for the disulfonyl fluoride is disclosed.

U.S. Pat. No. 4,973,429 discloses organic compositions having NLO properties. The organic compositions are in the form of a film and contain compounds of the formula:

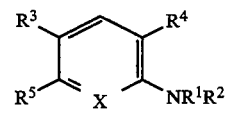

where X is $=\!CH\!-$ or $=\!N\!-$, $R^1$ is $C_{12}$-$C_{30}$-alkyl, $R^2$ is hydrogen or $C_1$-$C_{30}$-alkyl, $R^3$ is $-NO_2$, $-CN$, $-CF_3$, $-COCF_3$, $-SO_2CH_3$ or $-SO_2CF_3$, $R^4$ is hydrogen or is defined in the same way as $R^3$, $R^5$, hydrogen or $-NR^6R^7$ and $R^6$ and $R^7$ independently of one another are hydrogen or $C_1$-$C_{30}$-alkyl, it also being possible for any of the alkyl radicals to be partially fluorinated or perfluorinated.

U.S. Pat. No. 5,006,729 discloses a NLO compound comprising an electron donor group linked to an electron acceptor group by a $\pi$-conjugated group. The electron acceptor is a sulfone group containing a substituent selected from the group consisting of alkyl, hydroxyalkyl, and alkyl(meth-)acrylate moieties. The sulfone group is represented by the formula:

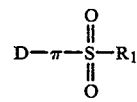

where D is the electron donor group, $\pi$ represents the conjugated group, and $R_1$ is one of the noted substituents.

The use of D, $R_1$, and $R^1$-$R^7$ above to describe the compounds disclosed in U.S. Pat. Nos. 4,973,429 and 5,006,729 is not to be confused with the use of similar notation below to describe the present invention.

SUMMARY OF THE INVENTION

This invention provides a new composition of matter for generating second-order NLO responses. The new composition comprises PDFMs incorporated in and aligned noncentrosymmetrically in an optically clear polymeric composition.

In another aspect, this invention provides a process for preparing a NLO composition, which comprises incorporating PDFMs in an optically clear polymer and aligning the incorporated PDFMs noncentrosymmetrically.

In a further aspect, this invention provides a method of generating a second-order NLO response, which comprises passing light through a NLO composition containing an optically clear polymeric composition having PDFMs incorporated therein and being aligned noncentrosymmetrically. Preferred light wavelengths for use with the NLO compositions of this invention range from about 400 to 2000 nm, more preferably from 600 to 1600 nm.

In a still further aspect, this invention provides a polymer having a plurality of polar moieties covalently bonded thereto, the polar moieties comprising: an electron-withdrawing group comprising a disulfone group; an electron-donating group; and a conjugated group located between the electron-withdrawing and donating groups.

In an additional aspect, this invention provides new PDFMs and a new process for preparing PDFMs. The new PDFMs are described below in the detailed description of this invention. The new process for preparing PDFMs comprises reacting vinyl ether disulfone molecules, enamine disulfone molecules, or alkenyl disulfone molecules having an activated methyl or methylene group with molecules having an electron-donating group, with the provisos that: (i) if the reactants include vinyl ether disulfone molecules, the molecules having the electron-donating group include activated aromatic molecules, activated heterocyclic molecules, dye bases, or dye olefins; (ii) if the reactants include enamine disulfone molecules, the molecules carrying the electron-donating group include dye bases or dye olefins; and (iii) if the reactants include alkenyl disulfone molecules having an activated methyl or methylene group, the molecules having the electron-donating group include aldehydes or acetals derived therefrom.

In this invention, it has been discovered that an optically clear polymeric composition having PDFMs incorporated therein will provide second-order NLO effects when the PDFMs have been aligned noncentrosymmetrically. It has also been discovered that the PDFM-incorporated compositions absorb light over a relatively narrow band of wavelengths. The latter discovery is particularly significant, because it is very desirable that minimal amounts of light be absorbed by the NLO compositions at the preferred wavelengths at which the NLO compositions operate. Having this advantage, the NLO compositions of this invention will be useful over a relatively greater range of wavelengths for NLO applications.

As used herein:

"disulfone-functionalized" and "disulfone group" means a molecular group having two —SO$_2$— radicals attached to the same carbon atom;

"dye base" means a compound derived from a quaternized heterocyclic ammonium salt and containing an electrophilically-reactive olefinic methylene or methine group conjugatively located to the nitrogen atom of the ammonium salt;

"dye olefin" means a 1,1-diaryl ethylene having an electron-donating group conjugatively located to the ethylene group, wherein the olefinic methylene group is electrophilically reactive;

"electron-donating" means a group that contributes to the electron density of a $\pi$-electron system;

"electron-withdrawing" means a group that attracts electron density from a $\pi$-electron system;

"optically clear" means possessing an attenuation of less than five (5) decibels per centimeter (dB/cm); and "polar" means possessing a dipole moment.

BRIEF DESCRIPTION OF THE DRAWINGS

FIG. 1 is a schematic representation of an apparatus for generating and detecting second harmonic light.

FIG. 2 is a schematic representation of an apparatus for providing electro-optic modulation of polarized light.

DETAILED DESCRIPTION OF PREFERRED EMBODIMENTS OF THE INVENTION

In a preferred embodiment, the present invention includes a NLO composition having PDFMs incorporated in an optically clear polymeric composition, where the incorporated PDFMs are aligned noncentrosymmetrically and have (i) an electron-withdrawing group comprising a disulfone group, (ii) an electron-donating group, and (iii) a conjugating group located between the electron-withdrawing and donating groups. The conjugating group preferably has from 1 to 6 double bonds, more preferably from 2 to 5 double bonds. As the term is used herein, "double bonds" includes the "resonance bonds" of aromatic and heteroaromatic nuclei, represented in the Kekulé fashion.

The electron-donating nature of a chemical may be determined by a variety of methods. The Hammett sigma value ($\sigma$) is an accepted measure of a group's electron-donating ability, especially the sigma para value ($\sigma_p$) under conditions of conjugation as shown, for example, by O. Exner in "Advances in Linear-Free-Energy Relationships", edited by N. B. Chapman and J. Shorter, Plenum Publ., N.Y., N.Y. (1972), particularly pages 28–30, 41–45, and 50–52. A group in the para-position that has a $\sigma_p$ value less than zero has an electron-donating ability that is useful in the present invention. It is preferred, however, that the electron-donating group of the PDFM have a $\sigma_p$ value of less than −0.3, more preferably less than −0.5. An electron-donating group in the ortho-position is also useful in the present invention, though somewhat less so, as a rule.

The PDFMs may be represented by the Formula:

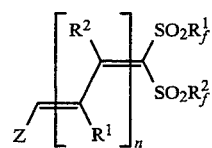

I where n is 0, 1 or 2, preferably 1 or 2;

$R^1$ and $R^2$ each independently represent hydrogen, an alkyl group of about 1 to 4 carbon atoms (for example, methyl, ethyl, propyl, isopropyl, butyl, and sec-butyl), or taken together in conjunction with the catenary carbon atoms therebetween form a 5 or 6-membered carbocyclic or heterocyclic ring, when n is 2, and $R^1$ and $R^2$ may variously combine with the catenary carbon atoms to form a 5 or 6-membered carbocyclic or heterocyclic ring(s) (viz., $R^1$ and $R^2$, $R^1$ and $R^1$, or $R^2$ and $R^2$, may combine with the catenary carbon atoms to form the 5 or 6 membered carbocyclic or heterocyclic ring(s));

$R_f^1$ and $R_f^2$ each independently represent fluorine, a saturated fluorinated alkyl group containing 1 to 10 carbon atoms, preferably 1 to 4 carbon atoms, or taken together in conjunction with the disulfone group may represent a 5, 6, or 7-membered ring containing two, three, or four carbon atoms, respectively, which are fluorinated, preferably highly fluorinated, more preferably perfluorinated (perfluorinated means that all hydrogen atoms bonded to carbon atoms have been replaced with fluorine atoms);

and Z represents: an aryl group that bears an electron-donating substituent; an activated heterocyclic aromatic group; a group derived from a dye base; or a group derived from a dye olefin.

No particular double bond geometry (for example, cis or trans) is intended by the structure of Formula I or any of the other formulas shown below.

When $R_f^1$ and $R_f^2$ represent saturated fluorinated alkyl groups of 1 to 10 carbon atoms, there may also be atoms other than fluorine bonded to the carbon atoms, such as halogens (for example, chlorine) or hydrogen. It is preferred that a majority of the carbon atoms adjacent and next-adjacent to the —$SO_2$— groups in $R_f^1$ and $R_f^2$ be fluorinated, and more preferably be perfluorinated. Preferably, not more than one atom bonded to each carbon atom is not a fluorine atom. More preferably, $R_f^1$ and $R_f^2$ are $CF_3$, especially when a molecular weight limitation exists, as for example, when attempting to maximize the number of NLO-active molecular groups per unit volume of the NLO composition. A saturated fluoroaliphatic group may be a straight or branched chain, cyclic, or a straight chain including a cyclic group. Additionally, the fluoroaliphatic group may contain an oxygen atom linking two carbon atoms, for example, —$CF_2OCF_2$—, or a nitrogen atom linking three carbon atoms, for example, (—$CF_2(CF_3)NCF_2$—). Exemplary fluoroaliphatic groups include perfluoromethyl, perfluoroisopropyl, perfluorobutyl, perfluorooctyl, perfluorododecyl, perfluoro-(4-ethylcyclohexyl), omega-chloroperfluorohexyl), 2-hydroperfluoropropyl, and perfluoro-(3-N-morpholinopropyl). In addition, and as noted above, $R_f^1$ and $R_f^2$ may be joined to form groups such as —$CF_2$—$CF_2$—, —$CF_2$—$CF_2$—$CF_2$—, and —$CF_2$—$CF_2$—$CF_2$—$CF_2$—. In such cases, a 5, 6, or 7-membered ring results.

When Z represents an aryl group that is substituted with an electron-donating group, that group may be represented by the Formula:

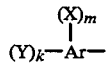

II where

Ar- represents a monovalent aryl group having 6 to 10 ring atoms;

Y represents a monovalent electron-donating substituent group having up to about 20 atoms (preferably conjugatively located relative to the conjugated system extending between the electron donating and electron withdrawing groups) such as an amino group represented by the formula $R^3R^4N$—, an ether or thioether group having the formula $R^3O$— or $R^3S$—, where $R^3$ and $R^4$ independently represent a monovalent alkyl of 1 to 12 carbon atoms (preferably 1 to 4 carbon atoms), cyanoalkyl of 1 to 4 carbon atoms (preferably cyanomethyl or cyanoethyl), an aryl, alkaryl, or arylene group having 6 to 10 ring atoms (preferably phenyl, tolyl, or phenylene) and having less than about 15 total carbon atoms, an alkylene, alkyleneoxy, alkylene-tert-amino, or alkylenethio group of 1 to 3 carbon atoms, an alkyleneacylamino having 1 to 3 ring atoms, an aralkyl group (such as benzyl) of up to about 15 total carbon atoms, or $R^3$ and $R^4$ taken together in conjunction with the nitrogen atom (and optionally adjacent positions on the conjugated aromatic ring) form one or more 5 or 6-membered heterocyclic rings;

X represents a monovalent substituent group having 1 to about 20 atoms, for example, a halo such as fluoro, chloro, bromo, or iodo, a substituted or unsubstituted aryl group Ar- as defined above, where Ar- may be substituted (for example, with an electron-donating group Y as defined above) a lower alkyl or a substituted lower alkyl having from 1 to 4 carbon atoms such as methyl, ethyl, propyl, isopropyl, butyl, and 4-chlorobutyl, an alkoxy group having from 1 to 4 carbon atoms such as methoxy, ethoxy, n-propoxy, or isopropoxy, a haloalkyl having from 1 to 4 carbon atoms such as 4-chlorobutyl or chloromethyl, an acyloxy group having from 1 to 4 carbon atoms such as acetoxy or buryfoxy, an acylamido having from 1 to 10 carbon atoms such as N-ethyl acetamido, saturated cyclics or heterocyclics having from 3 to 10 carbon atoms such as 2,3-methylenedioxy, 2,3-trimethylene, or 2,3 tetramethylene, an alkylthio group having from 1 to 10 carbon atoms such as methylthio, ethylthio, propylthio, acetylthio, an aryl or substituted aryl having 6 to 10 ring atoms such as phenyl, m-tolyl, p-anisyl, an aralkyl group having from 7 to 15 carbon atoms such as benzyl, an alkenyl having 2 to 15 carbon atoms, or an aralkenyl group having from 8 to 15 carbon atoms, for example β-styryl, allyl, etc.;

k is 1 or 2, preferably 1; and m is an integer of 0 to 6 ("0" is considered herein to be an integer).

It is to be understood that, when k is 2, or m is 2 or greater, each Y and each X, respectively, may be different from each other. For example, if k is 2, a first Y could be $(C_2H_5)_2N$— and a second Y could be $C_2H_5O$—.

Examples of aryl groups of the Formula II include 4-dimethylamino-1-naphthyl, 6-chloro-4-diethylamino-1-naphthyl, 2,4,5-trimethoxyphenyl, 2-fluoro-4-dimethylaminophenyl, 3-fluoro-4-dimethylamino-5-ethoxyphenyl, 3,4-methylenedioxyphenyl, 2-chloro-4-N-pyrrolidinophenyl, N-butyl-5-indolino, N-ethyl-6-(1,2,3,4,-tetrahydro)quinolino, N'-(2''-ethylhexyl)-4(N-piperazino) phenyl, 2,4-bis(methylthio)phenyl, 2-methyl-4-(4'-methylpiperidino)phenyl, 4-(N-2'-chloroethyl-N-propylamino)phenyl, 4-(N-methylacetamido)phenyl, 2-(N-piperidino)phenyl, 4-(N'-phenylpiperazino)phenyl, 4-(N-morpholino)phenyl, 4-(N-pyrrolidino)-3-fluorophenyl, and 4-julolidino.

when Z represents an activated heterocyclic aromatic group, that group may be represented by the Formula:

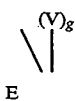

III where

E — represents a monovalent heterocyclic aromatic nucleus containing 5 or 6 ring atoms;

V represents X, or, taken together with atoms in the monovalent heterocyclic nucleus, V represents the necessary atoms to complete a 6-membered aromatic nucleus;

g is an integer of 0 to 4;

and E is S, O, or $NR^5$, preferably $NR^5$, where $R^5$ represents a substituent containing up to about twenty carbon atoms (preferably 1 to 10, more preferably 1 to 4), preferably selected from the group consisting of: an acyclic hydrocarbon substituent (substituted or unsubstituted) preferably aliphatic such as an alkyl group (including substituted alkyl) preferably containing from 1 to 13 carbon atoms, for example, methyl, ethyl, propyl, isopropyl, butyl, sec-butyl, hexyl, cyclohexyl, decyl, dodecyl, octadecyl, alkoxyalkyl (for example, methoxyethyl), hydroxyalkyl (for example, ω-hydroxyethyl, ω-hydroxypropyl, etc.); an alkenyl substituent such as allyl, 1-propenyl, 2-propenyl, 1-butenyl, 2-butenyl and 3-butenyl, etc.; an alkaryl substituent such as benzyl and β-phenylethyl; and an aryl substituent such as phenyl, p-tolyl, o-tolyl, 3,4-dichlorophenyl, paramethoxyphenyl, etc.

Representative examples of activated heterocyclic aromatic groups include N-butyl-2,4,5-trimethylpyrrolo, N-(3,4-dichlorophenyl)-2,5-dimethylpyrrolo, N,2-dimethyl-3-indolo, 5-dimethylamino-2-thienyl, 4,5-dimethyl-2-thienyl, N-(2'-cyanoethyl)-2,5-dimethyl-3-indolo, and N-methyl-2,5-diphenylpyrrolo.

When Z represents a group derived from a dye base, that group may be represented by the Formula:

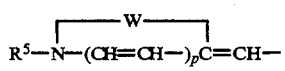

where p is 0, or 1; $R^5$ is as defined above; and

W represents the non-metallic atoms required to complete a heterocyclic nucleus containing from 5 or 6 atoms in the heterocyclic ring, which may also include in addition to the hetero nitrogen atom, a second hetero atom such as a second nitrogen atom, an oxygen atom, a selenium atom, or a sulfur atom. W also can be further substituted, for example, to form additional rings on the heterocyclic nucleus.

Representative heterocyclic nuclei from which the heterocyclic group may be derived include: a thiazole nucleus, for example, thiazole, 4-methylthiazole, 4-phenyl-thiazole, 5-methylthiazole, 5-phenylthiazole, 4,5-dimethylthiazole, 4,5-diphenylthiazole, 4-(2-thienyl)-thiazole, etc.); a benzothiazole nucleus (for example, benzothiazole, 4-chlorobenzothiazole, 5-cblorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenyl-benzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, etc.); a naphthothiazole nucleus (for example, α-naphthothiazole, β-naphthothiazole, 5-methoxy-β-naphthothiazole, 5-ethoxy-β-naphthothiazole, 8-methoxy-α-naphthothiazole, 7-methoxy-α-naphthothiazole, etc.); a thianaphtheno-7', 6', 4,5-thiazole nucleus (for example, 4'-methoxythianaphtheno-7', 6', 4,5-thiazole, etc.); an oxazole nucleus (for example, 4-methyloxazole, 5-methyloxazole, 4-phenyloxazole, 4,5-diphenyloxazole, 4-ethyloxazole, 4,5-dimethyloxazole, 5-phenyloxazole, etc.); a benzoxazole nucleus (for example, benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 5-methoxybenzoxazole, 5-ethoxybenzoxazole, 6-chlorobenzoxazole, 6-methoxybenzoxazole, etc.); a naphthoxazole nucleus (for example, α-naphthoxazole, β-naphthoxazole, etc.); a selenazole nucleus (for example, 4-methylselenazole, 4-phenylselenazole, etc.); a benzoselenazole nucleus (for example, benzoselenazole, 5-chlorobenzoselenazole, 5-methoxybenzoselenazole, 4,5,6,7-tetrahydrobenzoselenazole, etc.); a naphthoselenazole nucleus (for example, α-naphthoselenazole, β-naphthoselenazole, etc.); a thiazoline nucleus (for example, thiazoline, 4-methylthiazoline, etc.); a 2-quinoline nucleus (for example, quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 3,4-dihydro-3,3-dimethylquinoline, etc.); a 4-quinoline nucleus (for example, quinoline, 6-methoxyquinoline, 7-methylquinoline, 8-methylquinoline, etc.); a 1-isoquinoline nucleus (for example, isoquinoline, 3,4-dihydroisoquinoline, etc.); a 3-isoquinoline nucleus (for example, isoquinoline, etc.); a 3,3-disubstitutedindolenine nucleus (for example, 3,3-dimethylindolenine, 3,3,5-trimethylindolenine, 3,3,7-trimethylindolenine, etc.); a 2-pyridine nucleus (for example, pyridine, 3-methylpyridine, 6-methylpyridine, 5-ethylpyridine, 3,5-dimethylpyridine, 3-chloropyridine, 5-phenylpyridine, etc.); a 4-pyridine nucleus (for example, 2-methylpyridine, 3-methylpyridine, 3-chloropyridine, 2,6-dimethylpyridine, etc.); a 1-alkyl-2-imidazole nucleus (for example, 1-methylimidazole, 1-ethyl-4-phenylimidazole, 1-butyl-4,5-dimethylimidazole, etc.); a 1-alkyl-2-benzimidazole nucleus (for example, 1-methylbenzimidazole, 1-butyl-4-methyl-benzimidazole, 1-ethyl-5,6-dichlorobenzimidazole, etc.); a 1-alkyl-2-naphthimidazole nucleus (for example, 1-ethyl-α-naphthimidazole, 1-methyl-β-naphthimidazole, etc.); and an imidazoquinoxaline nucleus (for example, an imidazo[4,5-b]quinoxaline.

When z represents a group derived from a dye olefin, that group may be represented by the formula:

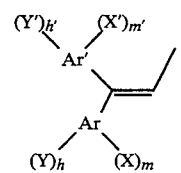

where Ar, Y, X, and m are as defined above; Ar' independently represents Ar (that is, Ar' may be the same or different from Ar) Y' and X' independently represent Y and X, respectively; m' independently represents m, and h and h' independently represent 0, 1, or 2, preferably 1, with the proviso that both h and h' cannot be zero. It being understood that when h and h' are equal to 2, and m' is 2 or greater, each Y, Y' and X', respectively, may be different from each other.

Representative examples of dye olefin groups include: 2-phenyl-2-(4'-N,N-diethylaminophenyl)vinyl; 2-(4'-ethoxyphenyl)-2-(4''-N,N-dimethylaminophenyl)-vinyl; and 2,2-bis-(4'-N,N-dimethylaminophenyl)vinyl.

PDFMs may be incorporated into a polymeric composition by (1) molecularly dispersing the PDFMs in the polymeric composition (a guest-host relationship), or (2) chemically reacting the PDFMs with a polymeric composition or with precursors to a polymeric composition. As the term is used herein, "incorporated" means the PDFMs are placed in a polymeric composition by either of these two methods.

In the first method, guest PDFMs may be incorporated into a host polymeric composition by, for example, forming a solution containing guest PDFM molecules, host polymeric composition, and solvent. The solution can be formed in a variety of ways; for example, PDFMs may be dissolved in a suitable solvent followed by adding a host polymer (or the order can be reversed), or the PDFMs and a host polymer may be dissolved together in a solvent. Suitable solvents may include organic solvents such as 1,2-dichloroethane, butyl acetate, acetone, chlorobenzene, chloroform, and mixtures thereof. After the solution is formed, the NLO molecules can be aligned noncentrosymmetrically by, for example, applying the solution to a substrate, removing the solvent, and poling the polymeric composition with a DC electric field. These steps are described below in more detail.

It may also be possible to incorporate guest PDFMs into a host polymeric composition without using a solvent. This might be accomplished, for example, by dissolving guest PDFMs in a molten host polymer, or by dissolving PDFMs in monomers that react to form a host polymer.

Any optically clear polymeric composition may be employed as a host in the NLO guest-host compositions this invention. Preferred optically clear polymeric compositions form chemically and environmentally stable NLO compositions, and have a $T_g$ that is greater than the maximal temperature of use of the NLO composition. More preferred polymeric compositions have a $T_g$ that is about 30° C. higher (yet more preferably 50° C. higher) than the temperature at which the NLO compositions are used. It is preferred that the $T_g$ of the polymeric composition be greater than about 80° C. It is also preferred that the guest-host polymeric composition be one that remains in an amorphous and glassy state throughout use of the NLO composition. Polymeric compositions that are amorphous and glassy are those that exhibit a glass transition temperature and have no significant melting point or x-ray evidence of crystallinity.

Examples of polymeric compositions that may be suitable as optically clear polymeric hosts include: polymers and copolymers of acrylates such as polyacrylates and polymethacrylates such as poly(methylmethacrylate) (PMMA); epoxy resins; polystyrene and derivatives and copolymers thereof; polycarbonates such as bisphenol-A-polycarbonate and copolymers thereof; and glassy polyesters such as amorphous (unoriented) poly(oxyethyleneoxyterephthaloyl), poly(oxyethyleneoxycarbonyl-1,1,3-trimethylindan-3,5-ylene-1,4-phenylenecarbonyl), poly(oxyisophthaloyloxy-1,4-phenyleneisopropylidene-1,4-phenylene), poly(oxy-1,4-phenylenefluoren-9-ylidene-1,4-phenyleneoxysebacoyl), poly(oxy-1,3-phenyleneoxyisophthaloyl), poly(oxypropylen-oxycarbonyl-2,6-napthylenecarbonyli, or poly(oxy-2,2,4,4-tetramethyl-1,3-cyclobutyleneoxycarbonyltrans-1,4-cyclohexylenecarbonyl); and glassy polyurethanes and polyamides such as poly(oxyethyleneoxycarbonylimino-1,4-phenylenemethylene-1,4-phenyleneiminocarbonyl), poly(oxytrimethyleneoxycarbonylimino-1,4-phenyleneethylene-1,4-phenyleneiminocarbonyl), poly(iminoadipoylimino-1,4-cyclohexylenemethylene-1,4-cyclohexylene), poly(imino-1,3-phenyleneiminosebacoyl), poly(sulfonyl-1,3-phenyleneiminoadipoylimino-1,3-phenylene), or poly(iminohexamethyleneiminocarbonyl- 2,2'-biphenylenecarbonyl); and copolymers among the polyesters, polyamides, and polyurethanes. Other potentially-useful polymers are disclosed in J. Brandrup et al., *Polymer Handbook*, John Wiley and Sons, Inc. (1975). Weight percentages of guest PDFMs in the guest-host polymeric composition range from about 1 to 70 percent, preferably 10 to 30 percent.

In the second method, PDFMs may be incorporated into an optically clear polymeric composition through a chemical reaction(s), which results in the formation of a polymeric composition that has covalently-bonded, polar moieties that each have a disulfone group. It is preferred to incorporate the PDFMs into a polymeric composition by this method (as opposed to dispersing the PDFMs in a polymeric composition) because, after poling, the covalently-bonded polar moieties are better able to hold their aligned positions in the resulting polymeric composition. In a guest-host composition, the dispersed PDFMs have a greater tendency to rotate and lose their alignment.

PDFMs may become covalently bonded to a polymeric composition by, for example, reacting PDFMs with a polymer. In another embodiment, PDFMs may be reacted with precursors to a polymer. For example, PDFMs may be reacted with polymerizable molecules to form monomers possessing polar moieties containing disulfone groups. These monomers may then be polymerized to form a polymer that possesses polar moieties containing disulfone groups. The polymers resulting from these noted reactions have a plurality of polar moieties covalently bonded thereto. The polar moieties each have an electron-withdrawing group comprising a disulfone group, an electron-donating group, and a conjugated group located between the electron-withdrawing and donating groups. These resulting polymers are considered to be new compositions of matter.

PDFMs and a polymer may be reacted so that the polar moieties (with disulfone functionality) become covalently bonded to the backbone or side chains of the polymer. This may be accomplished, for example, by dissolving PDFMs with a reactively-compatible polymer in a suitable solvent and preferably warming this solution under an inert atmosphere such as dry nitrogen. The solution preferably is warmed to a temperature of from about 50° to 200° C. (120° to 400° F.). The reaction temperature may vary depending on, for example, the solvent used, the reactivity of the PDFMs, and the reactivity of the polymer. In one method of attachment, a base is added to catalyze the reaction and/or to neutralize acid generated in the course of the reaction. Preferred bases include anhydrous pyridine, anhydrous trialkyl amine, and/or other non-nucleophilic nitrogen bases. The reaction mixture then, preferably, is heated to or near the boiling point of the solvent. After the reaction is sufficiently complete (typically in about 1 to 24 hours), the reaction mixture is cooled, and product precipitation may be induced, preferably, by adding a non-solvent for the polymer, for example, an alcohol such as methanol or ethanol, or water where appropriate.

A variety of solvents may be used in a reaction between PDFMs and a polymer. The solvent selected preferably dissolves the PDFMs and polymer and is not deleterious to the reaction. Preferably, the solvent is an organic solvent such as tetrahydrofuran, ethyl or butyl acetate, 1,4-dioxane, 1,2-dichloroethane, chloroform, acetonitrile, toluene, or a mixture thereof.

A polymer selected as a reactant preferably is one that forms an optically-clear polymeric composition having a polar disulfone functionalized moiety attached thereto. Representative examples of polymers that may be useful for reactions with PDFMs include (but are not limited to): reactive vinyl polymers (including copolymers) such as polyvinyl alcohol, poly(styrene-co-maleic anhydride), poly(methylvinylether-co-monobutylmaleate), poly(methylmethacrylate-co-methacrylic acid), and polymers (including copolymers) of acrylic acid, methacrylic acid, hydroxyethyl acrylate, hydroxyethyl methacrylate, isocyanatoethyl methacrylate, acryloyl chloride, and methacryloyl chloride; condensation polymers such as polysiloxanes, polyesters, and polyamides possessing further reactive sites, for example, poly(methyl-3-aminopropylsiloxane), and copolymers thereof such as poly(dimethylsiloxane-co-methyl-3-aminopropyl siloxane); and reactive polypeptides and co-polypeptides such as poly(glutamic acid), and co-polypeptides thereof. Other representative examples of polymers include (but are not limited to) modified versions of reactive natural polymers such as cellulose, for example, (hydroxyethyl) cellulose, (hydroxypropyl) cellulose, and (carboxymethyl) cellulose.

As indicated above, a PDFM may be reacted with polymerizable molecules to form monomers possessing polar moieties that contain disulfone groups. These monomers can then be polymerized to form a polymeric composition of this invention. This method may be accomplished, for example, by reacting a PDFM, such as, 1,1-bis(trifluoromethanesulfonyl)-2-(4-N-hydroxyethyl-N-ethylamino)phenyl)ethane, with a polymerizable molecule, for example, methacryloyl chloride, in a suitable solvent under an inert atmosphere. The newly-created monomer, a methacrylated PDFM, can be subsequently polymerized by a suitable polymerization mechanism, such as free radical polymerization, to produce a polymeric composition that contains polar moieties that each have a disulfone group.

Solvents suitable for the reaction between PDFMs and polymerizable molecules include the solvents described above for the reaction between the PDFMs and a polymer. Reaction temperatures are estimated to range from about 50° to 200° C. (120° to 400° F.), but may vary depending for example, the solvent used and the reactivity of the PDFMs and the polymerizable molecules.

Examples of other polymerizable molecules that may be used to form a PDFM-incorporated polymer include: reactively-substituted styrenes, such as parahydroxystyrene and chloromethylstyrene; acrylates and methacrylates such as 2-hydroxyethylacrylate, 2-hydroxyethylmethacrylate, and 2-aminoethylmethacrylate; and vinyl azlactones such as 2-vinyl-4,4-dimethyl-2-oxazolin-5-one (also called 2-vinyl-4,4-dimethylazlactone (VDM)), 2-isopropenyl-4,4-dimethyl-2-oxazolin-5-one, 2-vinyl-4,4-diethyl-2-oxazolin-5-one, 2-vinyl-4-ethyl-4-methyl-2-oxazolin- 5-one, 2-vinyl-4-dodecyl-4-methyl-2-oxazolin-5-one, 2-vinyl-4,4-pentamethylene-2-oxazolin-5-one, 2-vinyl-4-methyl-4-phenyl-2-oxazolin-5-one, 2-isopropenyl-4-benzyl-4-methyl-2-oxazolin-5-one, and 2-vinyl-4,4-dimethyl-1,3-oxazin-6-one; isocyanatoalkyl esters such as 2-isocyanatoethyl acrylate, and 2-isocyanatoethyl methacrylate; and isocyanate-functional monomers such as m- or p-isopropenylcumyl isocyanate (available from American Cyanamid, Stanford, Conn.) having the structural formula:

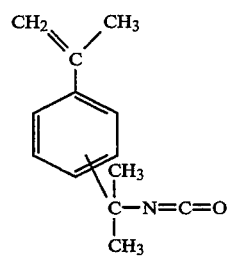

Useful azlactone monomers are described in U.S. Pat. No. 4,378,411 and in "Polyazlactones", Encyclopedia of Poly. Sci. and Engn., 1988 11, 558–571, 2nd Ed., Wiley, N.Y., both of which are incorporated here by reference.

Polymers possessing polar moieties that include disulfone groups may contain units represented by the Formula:

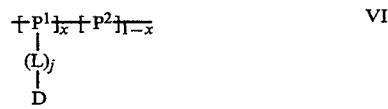

VI where $P^1$ and $P^2$ represent polymer main chain units; L is a linking group having 1 to 20 chain atoms, preferably 1 to 6; D is a polar moiety comprising a disulfone group, which polar moiety preferably comprises at least about 10 weight percent of the polymer, more preferably at least 30 weight percent; j is 0 or 1; and x represents the molar fraction of units —(L)$_j$—D bonded to the polymer backbone, preferably at least 0.01, more preferably at least 0.1, and even more preferably at least 0.3. At the upper end, x is preferably less than 0.8, and more preferably less than 0.5. Novel polymers of this invention preferably have a number average molecular weight that permits the polymer to form a film or layer. It is estimated that such polymers would have a molecular weight in the range of about 2,000 to 100,000.

Examples of linking groups L include (but are not limited to) organic groups containing ester, ether, thioether, alkylene, amide, carbonate, urethane, and urea moieties, and combinations and oligomers thereof, for example:

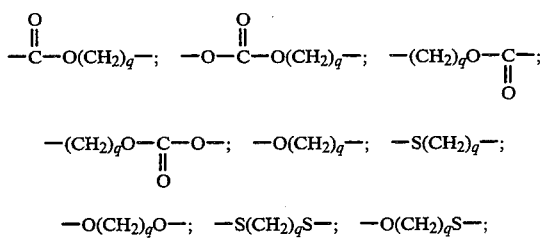

-continued

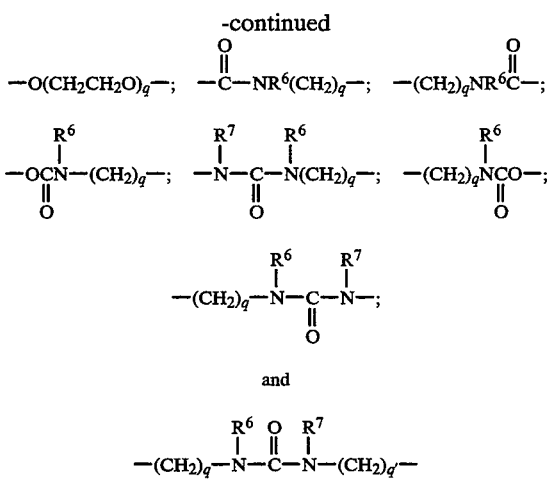

where: q and q' independently represent an integer of from 0 to 12, preferably 1 to 10, more preferably 2 to 8; and $R^6$ and $R^7$ independently represent H, or $C_rH_{2r+1}$, where r is an integer of from 1 to 4.

Polymeric compositions having PDFMs incorporated therein may be coated onto suitable substrates by known methods to form a layer of the polymeric composition. Suitable substrates may be inorganic, such as silicon wafers or glass, or may be organic, such as polymeric flat plates comprised of polymethylmethacrylate (PMMA), polycarbonates, epoxy resins, etc. An electrically-conductive substrate can serve as an electrode in an electro-optic device of the invention. Compositions having the PDFMs incorporated therein may be applied to a substrate, for example, in any of the ways known in the art, such as pouring, casting, roller coating, spraying, and spin coating. To apply a NLO composition to a substrate using these methods, the polymeric composition preferably is dissolved in a volatile solvent(s). Examples of solvents include organic polar solvents such as 1,2-dichloroethane, butyl acetate, acetone, chlorobenzene, chloroform, and mixtures thereof. Typical weight proportions of polymer in solution may range from about one to twenty percent or higher, as may be appropriate for the chosen application technique.

After applying the polymeric composition to a substrate, the solvent is removed, for example, by evaporation at room temperature, followed by controlled heating for several hours. Preferably, the polymeric composition is heated above to its $T_g$ to facilitate removal of the solvent. This heating preferably takes place in a vacuum oven.

The resulting composition (without the solvent) may be used on the substrate as a NLO device, or the composition may be removed from the substrate and used as a self-supporting NLO layer. Typically, it is preferred that the NLO layer be used on a substrate and have a uniform thickness. Adequate uniformity in a NLO layer typically can be achieved by having thickness variations of less than 5 micrometers, preferably less than 0.5 micrometers, and more preferably less than 0.05 micrometers. It is desired that the thickness variations be less than the wavelength of light passing therethrough. Uniformity is particularly desirable when light is passed through the layer in a direction parallel to the plane of the NLO layer. If the layer's thickness is not uniform in this instance, there is a possibility that the performance of the NLO device would be compromised in that light passing through the layer may sustain mode-mixing and might escape therefrom. Uniformity is not as essential when light is passed perpendicularly through the NLO layer.

It is also preferred that the NLO layer be transparent to incoming and outgoing light. If the applied layer is not transparent to incoming and outgoing light, the NLO device will absorb radiation; its effectiveness will be severely reduced, if not entirely lost. Adequate light transparency may be achieved by using a layer having an attenuation of not greater than five (5) dB/cm, preferably less than 1 dB/cm, for the chosen wavelengths of operation. Layer thicknesses generally range from about 0.1 to 10 micrometers, preferably from 0.5 to 3 micrometers.

Noncentrosymmetric alignment of the incorporated PDFMs may be accomplished by "poling" the polymeric composition under conditions favorable to molecular rotation. There are a variety of methods (known to those skilled in the art) to pole NLO compositions. Known methods include planar gap poling, sandwich electrode poling, and corona poling. In the planar gap method, the composition is placed in solution and is spin coated across a gap between two coplanar electrodes. The solvent is removed, and an external field is applied across the electrode gap at a temperature above the composition's $T_g$. Alternatively, the applied layer can be sandwiched between two electrodes to pole the PDFMs in a direction perpendicular to the plane of the applied layer, or a surface charge may be deposited by corona discharge onto the polymeric composition's surface. The incorporated PDFMs are preferably poled using a DC electric field to an extent that the poled composition's $\chi^{(2)}$ is measured to be about $10^{-9}$ electro static units (esu), preferably $10^{-7}$ esu, and more preferably $10^{-6}$ esu.

FIG. 1 shows an apparatus 10 for providing second harmonic generation of light. Light of frequency w from laser source 2 is incident on poled layer 4, and light of frequency 2w is created within layer 4, exits layer 4, and is subsequently detected. Two light beams exit layer 4, one at frequency 2w, and another at frequency w. The emerging light is successively passed through collection lens and color filter 6 to remove light of frequency w. Light of frequency 2w then passes through monochromator 8, and signal detector 12. The light of frequency 2w can be used for optical purposes such as optical memories, laser spectroscopy, photochemical reactions, or photo-reproduction. Other factors being appropriately controlled, the SHG intensity at frequency 2w provides a measure of the sheet's SHG $\chi^{(2)}$ effect. It is preferred that the light used for SHG be coherent and monochromatic.

FIG. 2 shows an apparatus for providing an electro-optic effect. Incident light (preferably monochromatic) of frequency w from laser 2 is successively passed through polarizer 22, phase compensator 24, focusing lens 26, and NLO layer 4 connected to modulation source 28. Light emerging from layer 4 is passed through collimating lens 30, polarization analyzer 32, and detector 34.

An applied electric field from modulation source 28 induces a birefringence in layer 4. The induced birefringence causes light polarizations parallel and perpendicular to the applied field to shift in phase with respect to one another. As the applied voltage is altered, the intensity of the light passing through the apparatus is also altered. This change in intensity as a function of the applied voltage provides a measure of the NLO layer's electro-optic $\chi X^{(2)}$ effect.

Compositions and devices disclosed above may be used for manipulating the direction, frequency, amplitude, and phase of light such as coherent monochromatic light from a laser. For example, the NLO composition of this invention can be applied to a substrate in the form of a uniform thin layer to produce a waveguide, or as noted above, the composition may be applied to a substrate to form a second harmonic generator or may be applied to a substrate and have electrodes attached thereto to form an electro-optic switch.

PREPARATION OF PDFMS

Known PDFMs have been prepared by methods disclosed in U.S. Pat. Nos. 3,932,526, 3,933,914, 3,984,357, 4,018,810, 4,069,233, and 4,156,696. The disclosures of these patents are incorporated here by reference. In the known methods, PDFMs are typically prepared by reacting an aldehyde and bis(perfluoroalkylsulfonyl)methane in a Knoevenagel reaction. The prior art methods are, however, limited in usefulness because the aldehyde reactants are costly or frequently unavailable and/or are troublesome or difficult to prepare. In the prior art methods, the aldehyde reactants typically are donor-substituted benzaldehydes or cinnamaldehydes or may be heterocycles or dye bases conjugatively bearing an aldehyde group. The following new method for preparing PDFMs avoids problems associated with the use of such aldehydes as starting materials.

In the new method, a vinyl ether disulfone molecule, an enamine disulfone molecule, or an alkenyl disulfone molecule is reacted with a molecule carrying an electron-donating group to form a PDFM. This new method is advantageous in that the disulfone reactant has a group comprising 1 to 3 double bonds attached to the disulfone group (the double bonds being conjugated when there is more than one). Using a disulfone reactant having such a molecular structure, prior art problems of attaching conjugated groups to the electron donating reactant are avoided.

When the disulfone reactant is a vinyl ether disulfone molecule, the molecule carrying the electron-donating group may be an activated aromatic compound, an activated heterocyclic compound, a dye base, or a dye olefin. As the term is used here, "activated" means the compounds are more susceptible to electrophilic substitution on the aromatic ring(s) than is anisole.

When the disulfone reactant is an enamine disulfone molecule, the reactant carrying the electron-donating group normally may not be an activated aromatic compound; however, a dye olefin or a dye base may be used to form a PDFM.

When using a dye base in a reaction with a vinyl ether disulfone or an enamine disulfone, it may be convenient to generate the dye base from a precursor in situ, for example, by reacting the dye base's hydrochloride with a base such as a tetraalkylammonium hydroxide, an alkali hydroxide, an amine, or the like, preferably an amine, and more preferably a tertiary amine.

When the disulfone reactant is an alkenyl disulfone molecule having at least two reactive allylic hydrogens as, for example, a vinylogous methyl group, the molecule carrying the electron-donating group may be an aldehyde or an acetal derived therefrom and preferably an aromatic aldehyde or an aromatic acetal derived therefrom: preferably having from 5 to 10 ring atoms, such as a substituted benzaldehyde, a "vinylog" thereof such as a cinnamaldehyde or acetals derived from such aldehydes. The aldehyde can also be a dye base aldehyde or a dye olefin aldehyde (that is, a dye base or a dye olefin bearing an aldehyde group on the active olefinic position) or acetals derived from such aldehydes. This reaction may be used when the molecule carrying the electron-donating group does not have an amine activating group, and especially when an aromatic acetal is available.

Described below are examples of reactions for forming PDFMs according to the method of this invention.

When the disulfone reactant is a vinyl ether disulfone molecule, a PDFM may be formed according to the following reaction schemes (ia–id):

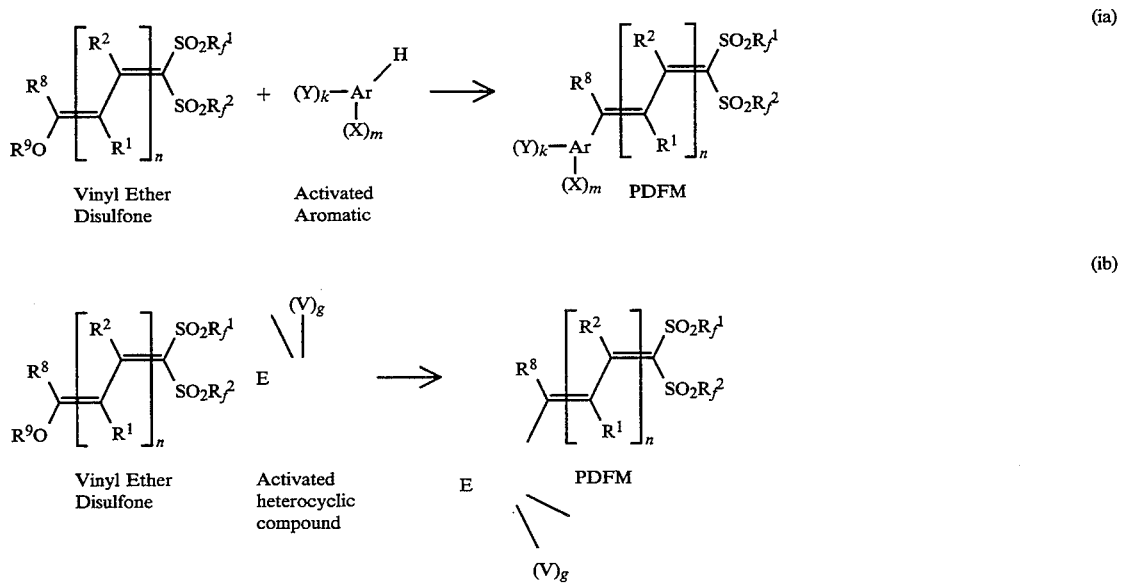

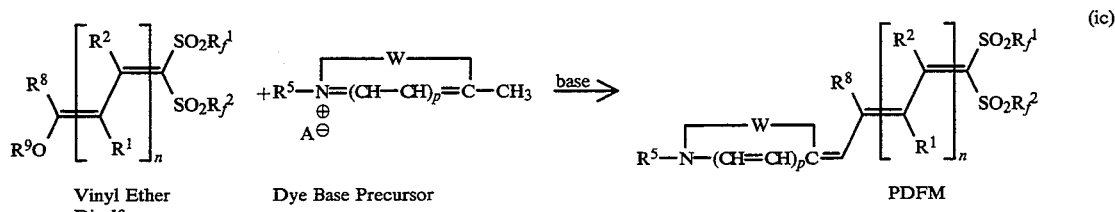

(ic)

Vinyl Ether Disulfone    Dye Base Precursor    PDFM

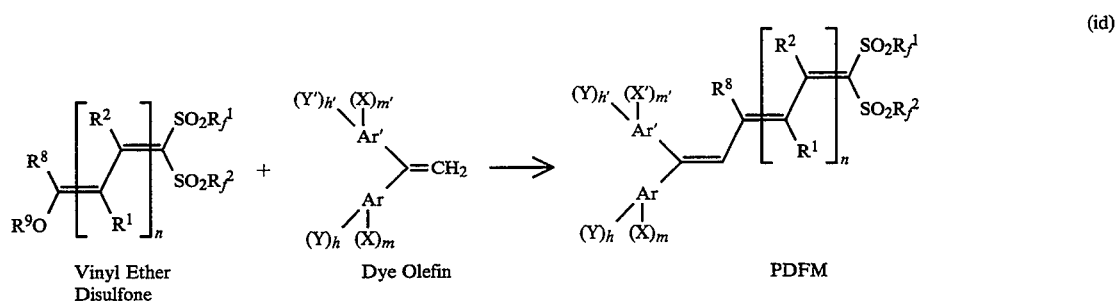

(id)

Vinyl Ether Disulfone    Dye Olefin    PDFM where $R^1$, $R^2$, $R_f^1$, $R_f^2$, $R^5$, W, Ar, Ar', X, Y, X', Y', h, h', m, m', g, n and p are as provided above, $R^8$ represents hydrogen or a monovalent organic radical, preferably a lower alkyl radical of 1 to 4 carbon atoms and more preferably hydrogen, $R^9$ represents a monovalent organic acyl, allyl, aryl, alkyl, or aralkyl radical, preferably having 1 to 8 carbon atoms, preferably an acyl or alkyl group, preferably from 1 to 4 carbon atoms, and $A^\ominus$ represents a monovalent anion, for example, chloride, bromide, iodide, p-toluenesulfonate, methylsulfate, methanesulfonate, tetrafluoroborate, and perchlorate. When $R^9$ represents an acyl, the disulfone reactant is essentially a vinyl ester disulfone; however, for purposes of simplicity, the term "vinyl ether disulfone" is used herein to include vinyl ester disulfones.

When the disulfone reactant is an enamine disulfone, a PDFM may be formed according to reactions (iia or iib):

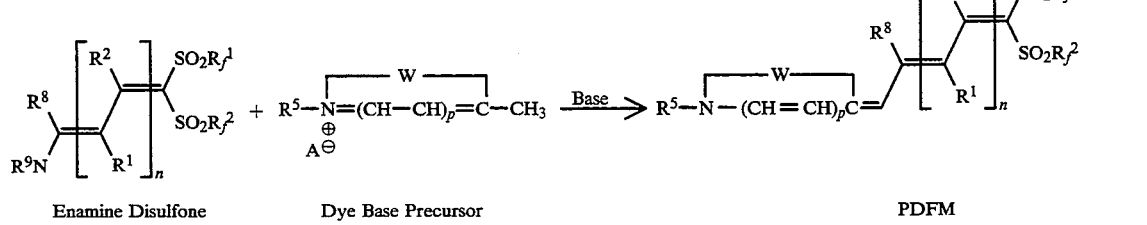

(iia)

Enamine Disulfone    Dye Base Precursor    PDFM

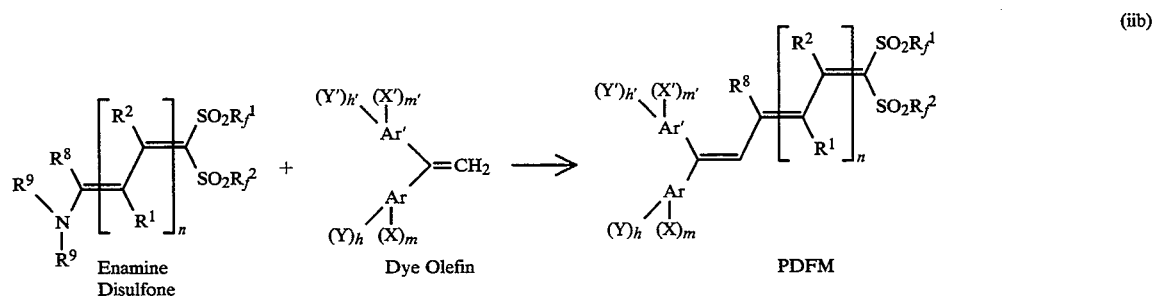

(iib)

Enamine Disulfone    Dye Olefin    PDFM where $R^1$, $R^2$, $R_f^1$, $R_f^2$, $R^5$, $R^8$, $R^9$, Ar, Ar', X, Y, X', Y', W, $A^\theta$, h, h', m, m', n, and p are as defined above.

When the disulfone reactant is an alkenyl disulfone having a methyl or methylene group, a PDFM may be formed according to reactions (iiia) and (iiib):

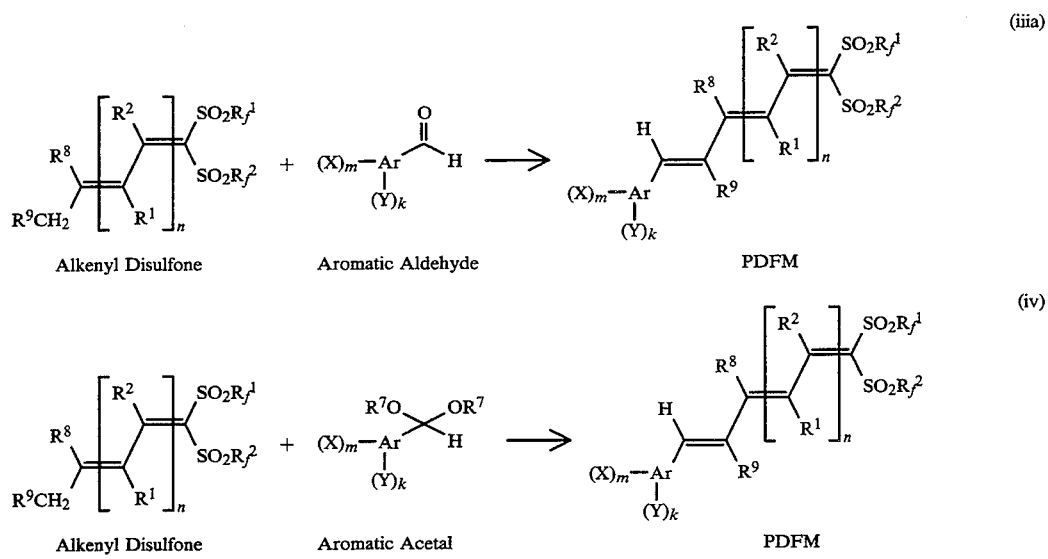

Alkenyl Disulfone    Aromatic Aldehyde    PDFM (iiia)

Alkenyl Disulfone    Aromatic Acetal    PDFM (iv)

where $R^1$, $R^2$, $R_f^1$, $R_f^2$, $R^7$, $R^8$, $R^9$, Ar, X, Y, k, m, n, and p are as described above.

In general, the above reactions (ia–iiib) will occur in the liquid phase at room temperature using a solvent that is capable of dissolving the reactants and is kinetically inert to them. Representative classes of such solvents include alkanes, such as halo- and polyhaloalkanes, aromatic hydrocarbons such as mono and polysubstituted aromatic compounds, acids, anhydrides, esters, and alcohols. Examples of such solvents include hexane, toluene, xylenes, chloroform, chlorobenzene, o-dichlorobenzene, ethyl acetate, acetic acid, acetic anhydride, and ethanol. Although the reactions proceed at room temperature, it is often advantageous and usually preferred to heat the reaction mixture to the boiling point of the solvent and to monitor the course of the reaction by thin layer chromatography (TLC). It is also possible in some situations to use a solvent that dissolves the starting materials but does not dissolve the final product. When such a solvent is used, the PDFM product precipitates during the reaction or upon cooling the reaction mixture. The product may then be isolated by filtration. Otherwise, (when the product is not insoluble in the solvent) the product may be isolated by cooling, removing solvent in vacuo, and recrystallizing the residue from another solvent.

The disulfone reactants used to form PDFMs may be prepared as follows. The vinyl ether disulfone may be prepared according to reactions (iva) and (ivb) provided below, the enamine disulfone may be prepared as described in U.S. Pat. No. 3,932,526, and the alkenyl disulfone may be prepared according to exemplary reaction (v) provided below.

A vinyl ether disulfone may be formed by reacting a bis(diacetal) such as malonaldehyde bis-(dimethyl acetal) (preferably named 1,1,3,3, tetramethoxypropane) or an orthoester such as triethyl orthoformate (Aldrich Chemical Co., Milwaukee, Wis.) with a methane disulfone (prepared as described in R. J. Koshar and R. A. Mitsch, J. Org. Chem. 1973 38, 3358–63 and U.S. Pat. No. 3,932,526) in an organic solvent such as acid anhydride, preferably acetic anhydride. These reactions are illustrated as follows:

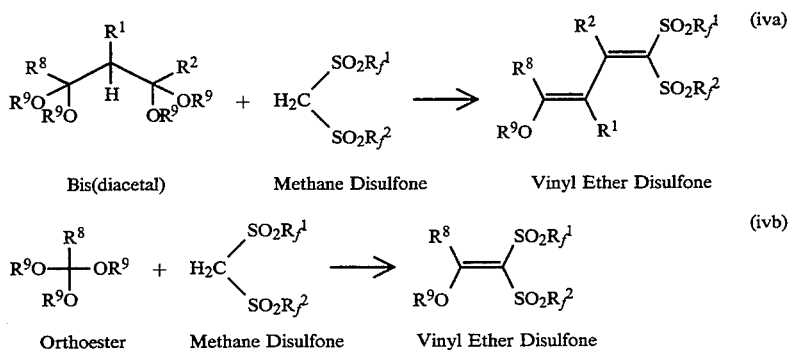

Bis(diacetal)    Methane Disulfone    Vinyl Ether Disulfone (iva)

Orthoester    Methane Disulfone    Vinyl Ether Disulfone (ivb)

where $R^1$, $R^2$, $R_f^1$, $R_f^2$, $R^8$, $R^9$, are as provided above. Reactions (iv) and (v) may occur at room temperature or at elevated temperatures. Elevated temperatures are preferred because there is a significant increase in the rate of reaction. In general, the reaction will be substantially complete at about 1 to 4 hours at temperatures above 50° C. Preferred reaction temperatures are at from 50° to 70° C. At room temperature, the vinyl ether disulfone is formed in about 20 to 50 hours. This reaction appears to go to completion, and therefore it is often beneficial to use the vinyl ether disulfone in situ to prepare a PDFM. Alternatively, if desired, the vinyl ether disulfone may be isolated by vacuum distillation before it is reacted with a molecule carrying an electron-donating group to form a PDFM.

When the vinyl ether disulfone is used in situ, the generation of vinyl ether disulfone is followed by cooling the mixture, adding an activated aromatic compound, an activated heterocyclic compound, dye base, or dye olefin and reacting the vinyl ether disulfone with the activated aromatic, activated heterocyclic compound, dye base, or dye olefin for a few minutes to 1–2 hours at from about room temperature to about 70° C. to form a PDFM. Some PDFMs have limited solubility in acid anhydrides such as acetic anhydride and in acetic acid and therefore will precipitate during the reaction. In this instance, the PDFMs can then be purified by filtration and washing or recrystallization using methanol or a methanol/water mixture. The reaction can be monitored by TLC if desired. When the PDFMs do not precipitate upon formation, they may be isolated by precipitation using aqueous methanol, or by solvent removal, and purified by recrystallization.

It is preferred to add the activated aromatic, dye base, dye olefin, or heterocyclic compound after the vinyl ether disulfone is formed. If all of the reagents are simply mixed together and heated, a low yield of PDFMs will usually result.

An alkenyl disulfone may be formed, for example, by reacting an aldehyde with a methane disulfone as shown in reaction (v):

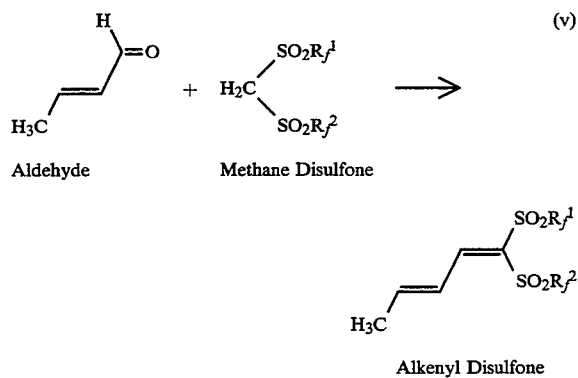

where $R_f^1$ and $R_f^2$ are as provided above.

This reaction may be carried out in solution using a solvent that is capable of dissolving the reactants and is kinetically inert to them. Representative classes of such solvents may include those that are provided above as being suitable in the reactions for forming PDFMs. Examples of such solvents are also provided above. The reactions will occur slowly at room temperature, but it is often preferred to heat the reaction to the boiling point of the solvent, and to remove the water as it is formed using, for example, a Dean-Stark trap. This reaction appears to go to completion. It therefore may be beneficial to use the alkenyl disulfone in situ to prepare PDFMs.

Representative examples of vinyl ether disulfones that may be used to prepare PDFMs include but are not limited to: $CH_3O—CH=C(SO_2CF_3)_2$; $CH_3O—CH=CH—CH=C(SO_2CF_3)_2$; $CH_3O—CH=C(SO_2F)_2$; $CH_3O—CH=CH—CH=C(SO_2F)_2$; $CH_3O—CH=C(SO_2C_8F_{17})_2$; $CH_3O—CH=CH—CH=C(SO_2C_8F_{17})_2$; $CH_3O—CH=C(SO_2CF_3)(SO_2C_8F_{17})$; $CH_3O—CH=CH—CH=C(SO_2CF_3)(SO_2C_8F_{16})$; $(CH_3O)(CH_3)C=C(SO_2CF_3)_2$; and $C_2H_5O—CH=C(SO_2CF_3)_2$.

Representative examples of enamine disulfones that may be used to prepare PDFMs include but are not limited to: $(CH_3)_2N—CH=C(SO_2CF_3)_2$; $(CH_3)_2N—CH=CH—CH=C(SO_2CF_3)_2$; $(CH_2)_4N—CH=C(SO_2CF_3)_2$; and $O(CH_2CH_2)_2N—CH=CH—CH=C(SO_2CF_3)_2$.

Representative examples of alkenyl disulfones that may be used to prepare PDFMs include but are not limited to: $CH_3—CH=C(SO_2CF_3)_2$; $CH_3—CH=CH—CH=C(SO_2CF_3)_2$; $CH_3—CH=C(SO_2C_8F_{17})_2$; $CH_3—CH=CH—CH=C(SO_2C_8F_{17})_2$; $CH_3—CH=C(SO_2F)_2$; $CH_3—CH=CH—CH=C(SO_2F)_2$; $CH_3—CH=C(SO_2CF_3)(SO_2C_8F_{17})$; and $CH_3—CH=CH—CH=C(SO_2CF_3)(SO_2C_8F_{17})$.

Representative examples of activated aromatic compounds that may be used to prepare PDFMs by reaction with vinyl ether disulfones include but are not limited to: N,N-dimethylaniline; N,N-diethylaniline; N,N-dipropyl aniline; N-phenyl-morpholine; julolidine; N,N-dimethyl-1-naphthylamine; N,N-diethyl-m-phenetidine; N,N-dimethyl-2,5-dimethoxyaniline; and N,N-dibutylaniline.

Representative examples of activated heterocycles that may be used to prepare PDFMs by reaction with vinyl ether disulfones include but are not limited to: N-methylindole; N-ethyl-2-phenylindole; and 1-p-anisyl-2,5-dimethylpyrrole.

Representative examples of dye bases and quaternary ammonium precursors of dye bases that may be used to prepare PDFMs by reaction with vinyl ether disulfones or enamine disulfones include but are not limited to: N-methyl-quinaldinium methylsulfate; N-methyl-lepidinium p-toluenesulfonate; N-ethyl-2-methylbenzothiazolinium iodide, 1,3,3-trimethyl-2-methyleneindolenine; and 1,3-diethyl-2-methylimidazo-[4,5b]quinoxalinium p-toluenesulfonate.

Representative examples of dye olefins that be used to prepare PDFMs by reaction with vinyl ether disulfones or enamine disulfones include but are not limited to: 1,1-bis-(4′-N,N-dimethylaminophenyl)ethylene; 1,1-bis-(4′-N,N-diethylaminophenyl)ethylene; 1-phenyl-1-(4′-N,N-diethylaminophenyl)ethylene (Chem. Abst. Serv. No. 115655-10-2, hereinafter cited as "CAS"); and 1-(4′-ethoxyphenyl)-1-(4″-N,N-dimethyl-aminophenyl-)ethylene (CAS 113915-69-8).

Examples of aldehydes that can be used to prepare PDFMs by reaction with alkenyl disulfones include but are not limited to: benzaldehyde; 4-methoxybenzaldehyde; mesitaldehyde; 2,3-dimethoxy-5-bromobenzaldehyde; 2,5-dimethoxybenzaldehyde; 2-isopropoxybenzaldehyde; 2,4,5-trimethoxybenzaldehyde; 4-methoxycinnamaldehyde; 4-pentyloxybenzaldehyde; 3-methyl-4-benzyloxybenzaldehyde; 4-(methoxymethyl)benzaldehyde; 1-naphthaldehyde; 2-naphthaldehyde; 9-anthraldehyde; tolualdehyde; 2-furaldehyde; thiophene-2-carboxaldehyde; and pyrrole-2-carboxaldehyde.

Representative examples of acetals that may be used to prepare PDFMs by reaction with an alkenyl disulfone include: 2-furaldehyde diethyl acetal; N,N-diethylaminobenzaldehyde diethyl acetal; N,N-dimethylaminobenzaldehyde diethyl acetal; p-methoxybenzaldehyde dimethyl acetal; and o-methoxybenzaldehyde diethyl acetal.

Representative examples of diacetals that may be used to prepare vinyl ether disulfones include: 1,1,3,3-tetramethoxypropane; 1,1,3,3,-tetraethoxypropane; and $(CH_3O)_2CH—CH_2—CH=CH—CH(OCH_3)_2$ (CAS 1116-86-5).

Representative examples of orthoesters that may be used to prepare vinyl ether disulfones include: triethyl orthoacetate; triethyl orthoformate; triethyl orthopropionate; trimethyl orthoacetate; trimethyl orthobenzoate; trimethyl orthobutyrate; trimethyl orthoformate; trimethyl orthovalerate; tripropyl orthoformate; and diethylphenyl orthoformate.

Representative examples of aldehydes that may be used to prepare the alkenyl disulfone molecules include but are not limited to: crotonaldehyde; acetaldehyde; propionaldehyde; butyraldehyde; and heptaldehyde. Other useful aldehydes can be found in *Organic Reactions*, v. 15, Chapter 2, (1967) A. C. Cope ed., New York, the disclosure of which is incorporated here by reference. The aldehydes selected should have at least two active hydrogen atoms.

Representative examples of PDFMs that may be formed by the above-described process of this invention are shown in Table 1. Some of these PDFMs may be formed by the prior art methods disclosed in U.S. Pat. Nos. 3,932,526, 3933,914, 3,984,357, 4,018,810, 4,069,233, 4,156,696, and 4,357,405. Whether prepared by the new method of this invention or prior art methods, all of the PDFMs appear to be useful for generating NLO responses.

New PDFMs of this invention may be represented by Formula I, where n, $R^1$, $R^2$, and Z are as defined above, and $R_f^1$ and $R_f^2$ taken together in conjunction with the disulfone group form a 5, 6, or 7-membered ring containing two, three, or four carbon atoms that are fluorinated, preferably highly fluorinated, more preferably perfluorinated.

New PDFMs of this invention also include compounds of the Formula I, where n, $R^1$, $R^2$, and are as defined above, and $R_f^1$ and $R_f^2$ independently represent fluorine, a saturated fluorinated alkyl group containing 1 to 10 carbon atoms, or taken together with the disulfone group form a 5, 6, or 7-membered ring containing 2, 3, or 4 carbon atoms, respectively, which are fluorinated, with the provisos that (i) at least one of $R_f^1$ and $R_f^2$ is fluorine, and (ii) n is 1 or 2 when Z is a group of the Formula II

and Y is $NR^3R^4$, where Ar, X, Y $R^3$, $R^4$, k, and m are as defined above.

Other new PDFMs are the vinyl ether disulfone molecules, which may be represented by the Formula VII:

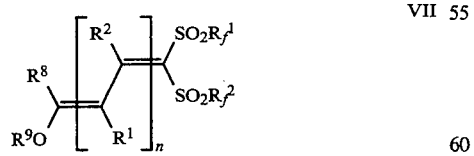

where $R^1$, $R^2$, $R^8$, and $R^9$, are as defined above, n is 0, 1, or 2, and $R_f^1$ and $R_f^2$ here independently represent fluorine, a saturated fluorinated alkyl radical containing 1 to 10 carbon atoms, or taken together in conjunction with the disulfone group form a 5, 6, or 7-membered ring containing 2, 3, or 4 carbon atoms, respectively, which are fluorinated.

Additional new PDFMs may be represented by the Formula VIII:

where $R_f^1$ and $R_f^2$ here independently represent fluorine, a saturated fluorinated alkyl radical containing 1 to 10 carbon atoms, or taken together in conjunction with the disulfone group form a 5, 6, or 7-membered ring containing 2, 3, or 4 carbon atoms, respectively, which are fluorinated, and $R^{10}$ is selected from the group consisting of:

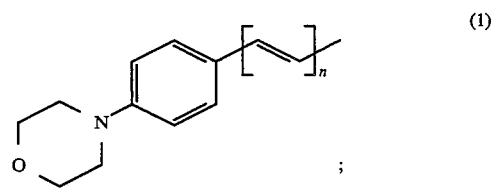

(1)

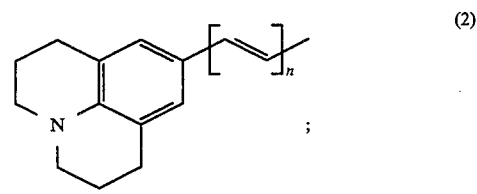

(2)

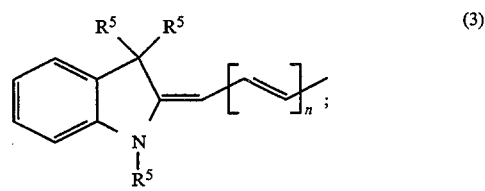

(3)

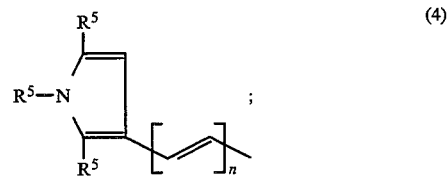

(4)

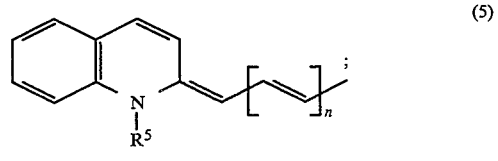

(5)

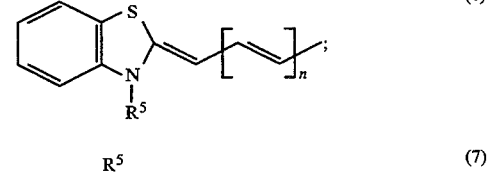

(6)

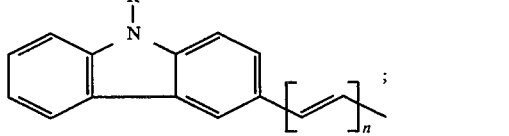

(7)

-continued

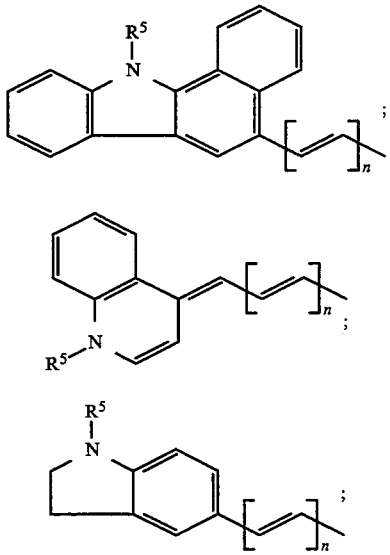

(8) 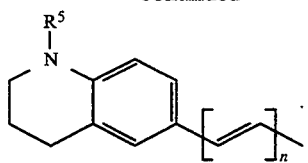

(9)

(10)

(11) 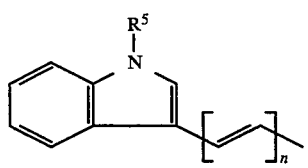

where n is 0, 1, or 2 and $R^5$ is as defined above.

Further new PDFMs are represented by the formula (12)

where n is 1 or 2 and $R^5$ is as defined above.

PDFMs 1–35 illustrated below in Table 1 were prepared in the following Examples 1–35, respectively. In Examples 1–35 the melting points were determined for some of the compounds. Where those melting points were determined, those values are shown in Table 1. If the melting point was not determined, "n/d" is provided in Table 1. If the compound decomposed at the melting point, "dec." indicates this.

TABLE 1

| Compound No. | Structure | Melting Point (°C.) |
|---|---|---|
| 1. | 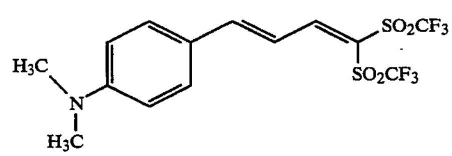 | 205–207 |
| 2. | 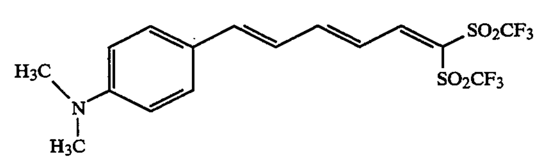 | 161–165 |
| 3. | 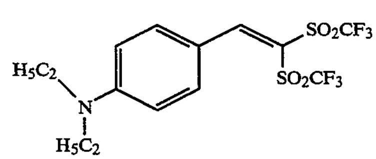 | 154–157 |
| 4. | 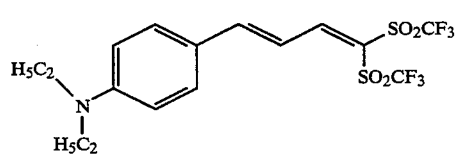 | 134–137 |
| 5. | 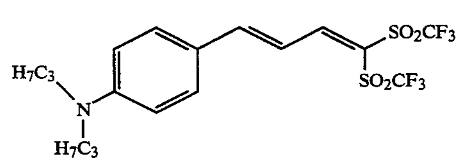 | 143–147 |

TABLE 1-continued
| Compound No. | Structure | Melting Point (°C.) |
|---|---|---|
| 6. | 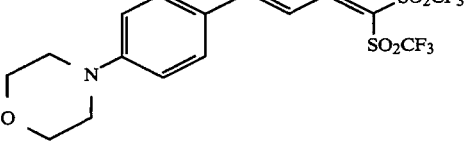 | 156–157 |
| 7. | 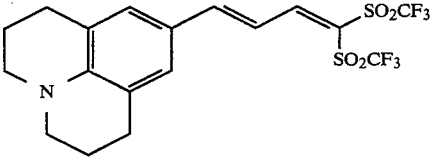 | 138–143 |
| 8. | 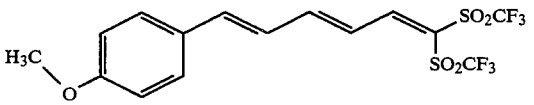 | 138–148 |
| 9. | 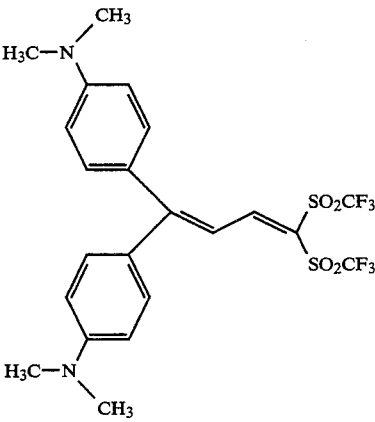 | 210 |
| 10. | 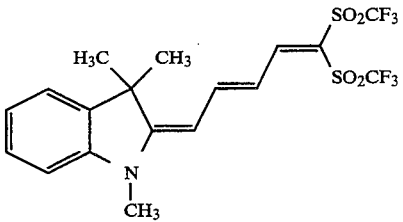 | 218 |
| 11. | 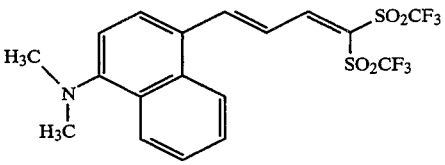 | 181–183 |
| 12 | 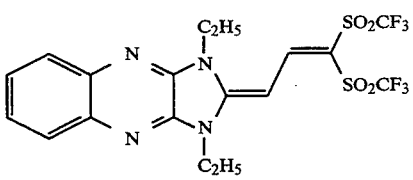 | 260–263 |

TABLE 1-continued

| Compound No. | Structure | Melting Point (°C.) |
|---|---|---|
| 13. | (4-Me₂N-C₆H₄)₂C=CH-CH=CH-C(SO₂CF₃)₂ | 148–153 (dec.) |
| 14. | 4-(Et₂N)-2-(EtO)-C₆H₃-CH=CH-CH=C(SO₂CF₃)₂ | 155–159 (dec.) |
| 15. | (4-Et₂N-C₆H₄)₂C=CH-CH=CH-C(SO₂CF₃)₂ | 171–173 (dec.) |
| 16. | 4-(Me₂N)-2,5-(MeO)₂-C₆H₂-CH=CH-CH=C(SO₂CF₃)₂ | n/d |
| 17. | (1-methylindol-3-yl)-CH=CH-CH=C(SO₂CF₃)₂ | 177–179 (dec.) |
| 18. | (1-methylindol-3-yl)-CH=C(SO₂CF₃)₂ | 255–257 |
| 19a. | 4-Me₂N-C₆H₄-CH=C(CH₃)-C(SO₂CF₂-CF₂-SO₂CF₂) | 204–206 |
| 19b. | 4-Me₂N-C₆H₄-CH=C-C(CH₃)(SO₂CF₂)(SO₂CF₂) | 213.5–214.5 |

TABLE 1-continued

| Compound No. | Structure | Melting Point (°C.) |
|---|---|---|
| 19c. | (structure) | 200–201 (dec.) |
| 20. | (structure) | 219–221 |
| 21. | (structure) | 158–163 |
| 22. | (structure) | 131–132 |
| 23. | (structure) | n/d |
| 24. | (structure) | 145–147 (dec.) |
| 25. | (structure) | 253–255 (dec.) |
| 26. | (structure) | 255–256 (dec.) |
| 27. | (structure) | 198–200 |

TABLE 1-continued

| Compound No. | Structure | Melting Point (°C.) |
|---|---|---|
| 28. | 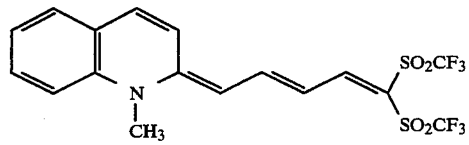 | 242–243 (dec.) |
| 29. | 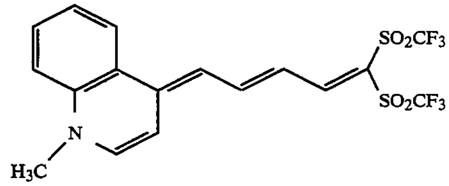 | 270–271 |
| 30. | 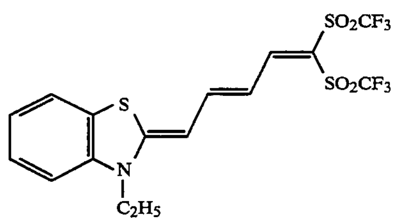 | 245–247 |
| 31a. | 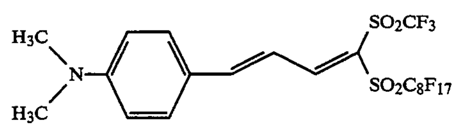 | 143–144 |
| 31b. | 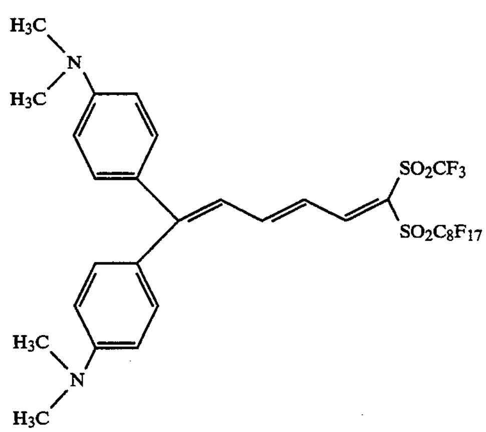 | 104–119 |
| 32. | 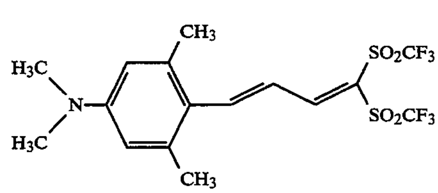 | 176–177 (dec.) |
| 33a. | 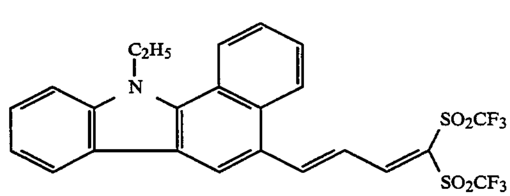 | n/d |

TABLE 1-continued

| Compound No. | Structure | Melting Point (°C.) |
|---|---|---|
| 33b. | (structure: NC-CH₂CH₂ and CH₃CH₂ on N attached to phenyl-CH=CH-CH=C(SO₂CF₃)₂) | n/d |
| 33c. | (structure: NC-CH₂CH₂ and CH₃CH₂ on N attached to 3-methylphenyl-CH=CH-CH=C(SO₂CF₃)₂) | n/d |
| 33d. | (structure: phenyl and CH₃ on N attached to phenyl-CH=CH-CH=C(SO₂CF₃)₂) | n/d |
| 33e. | (structure: two benzyl (PhCH₂) groups on N attached to phenyl-CH=CH-CH=C(SO₂CF₃)₂) | n/d |
| 33f. | (structure: two H₃CC(O)-OCH₂CH₂ groups on N attached to phenyl-CH=CH-CH=C(SO₂CF₃)₂) | n/d |
| 33g. | (structure: H₃CC(O)-OCH₂CH₂ and NC-CH₂CH₂ on N attached to phenyl-CH=CH-CH=C(SO₂CF₃)₂) | n/d |
| 33h. | (structure: two NC-CH₂CH₂ groups on N attached to phenyl-CH=CH-CH=C(SO₂CF₃)₂) | n/d |
| 33j. | (structure: N-phenylpyrrole attached to -CH=CH-CH=C(SO₂CF₃)₂) | n/d |
| 34. | (structure: bis(4-methylphenyl)amino-phenyl-CH=C(SO₂CF₃)₂) | n/d |

TABLE 1-continued

| Compound No. | Structure | Melting Point (°C.) |
|---|---|---|
| 35. | 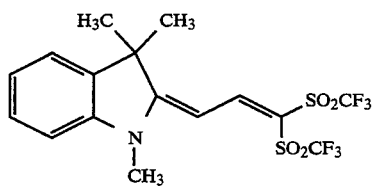 | 197–199 |

Objects and advantages of this invention are further illustrated in the following examples, but the particular materials and amounts thereof recited in these examples, as well as other conditions and details, should not be construed to unduly limit this invention.

EXAMPLES

In Examples A–J, starting materials were made, which were subsequently used in reactions to form PDFMs. In Examples A, B, C, and F–L, vinyl ether disulfones were prepared, and in Examples D and E, an alkenyl disulfone was prepared. In Examples 1–35, compounds 1–35 were prepared, respectively, using in many cases the novel method of the present invention. The structures assigned to each of the compounds 1–35 were determined using one or more of the following methods: IR spectroscopy; NMR spectroscopy; ultraviolet/visible spectroscopy; product mass balance, and elemental analysis. The PDFMs of this invention typically display solvatochromy.

Example A

Preparation of $(CH_3O)-CH=CH-CH=C(SO_2CF_3)_2$

To a 250 ml round-bottomed flask equipped with a magnetic stirrer, ice bath, condenser, and nitrogen atmosphere was added 8.21 g (0.05 mole) of 1,1,3,3, tetramethoxypropane (CAS 102-52-3) also known as malonaldehyde bis(dimethyl acetal). Acetic anhydride (10 g) was added slowly to minimize the resulting exotherm. The solution was cooled in ice, and a solution of 14.00 g (0.05 mol) of bis(trifluoromethylsulfonyl)methane (CAS 428-76-2), in 10 g of acetic anhydride, was added slowly. Upon completion of the addition, the cooling bath was removed, and the solution was allowed to warm to room temperature. A heating mantle was attached, and the solution was heated at reflux for 2 hr. The amber-red solution was cooled to room temperature. Each 2.12 g of this solution assumedly contained 0.0025 moles of the vinyl ether disulfone.

Example B

Preparation and Isolation of $(C_2H_5O)-CH=C(SO_2CF_3)_2$

Bis(trifluoromethylsulfonyl)methane (28.03 g, 0.10 mol) and 25 g (0.26 mol) of acetic anhydride were placed in a 100 ml round-bottomed flask equipped with a condenser and magnetic stirrer. Stirring was begun, the reactants dissolved, and the solution was cooled in an ice bath and stirred for 10 minutes. Triethylorthoformate, CAS 122-51-0, (14.8 g, 0.10 mol) was slowly added over 5 minutes. The ice bath was replaced with a cold water bath to slowly raise the temperature and moderate the exotherm. After 15 minutes, the water bath was removed and the yellow-orange solution was allowed to stir at room temperature for 1 hour. A heating mantle was attached, and the reaction mixture was heated at reflux for 2 hours. The solution was cooled to room temperature, and the solvent was removed at reduced pressure of afford a dark viscous oil. The crude material was isolated by vacuum distillation (bp 110°–117° C. at 1 mm) to afford 13.26 g (39%) of the vinyl ether disulfone.

Example C

Preparation and Isolation of $(CH_3O)-CH=CH-CH=C(SO_2CF_3)_2$

Bis(trifluoromethylsulfonyl)methane (28.01 g, 0.10 mol) and 20 g acetic anhydride were added to a 250 ml round-bottomed flask equipped with magnetic stirrer, ice bath, condenser, and nitrogen atmosphere. Stirring was begun, and upon dissolution of the bis(trifluoromethylsulfonyl)methane, the solution was cooled in an ice bath. A solution of 16.42 g (0.01 mol) of 1,1,3,3-tetramethoxypropane in 20 g of acetic anhydride was added in 5 g portions over 0.5 hour to minimize the exotherm. The solution turned orange-brown. Upon completion of the addition, the cooling bath was removed, and the solution warmed to room temperature. A heating mantle was attached, and the solution was heated at reflux for 2 hours. The dark amber-red solution was cooled to room temperature, and solvent was removed at reduced pressure to afford a dark viscous oil. The crude material was isolated by vacuum distillation (bp 130° C. at 0.3 mm); 25.51 g (73%) of the vinyl ether disulfone was produced.

Example D

Preparation of a Reaction Product Containing $CH_3-CH=CH-CH=C(SO_2CF_3)_2$

An alkenyl disulfone was prepared by placing 50 ml of toluene, 1.00 g of 85% crotonaldehyde (0.85 g, 0.01 mol (CAS 123-73-9)), 2.80 g (0.01 mole) of bis(trifluoromethylsulfonyl)methane, and about 1 g of anhydrous sodium sulfate (as a drying agent) in a 100 ml round-bottomed flask, equipped with magnetic stirrer, condenser, heating mantle, nitrogen atmosphere, and Dean-Stark trap. Stirring was begun, and the mixture was heated at reflux for 4 hr and was stirred overnight, to form the alkenyl disulfone, $CH_3-CH=CH-CH=C(SO_2CF_3)_2$, CAS 58510-89-7.

Example E

Preparation of a Reaction Product Containing $CH_3-CH=CH-CH=C(SO_2CF_3)_2$

The alkenyl disulfone $CH_3-CH=CH-CH=C(SO_2CF_3)_2$ was prepared by the method of Example D, except 100 ml of mixed hexanes were used in lieu of 50 ml of toluene, and no drying agent was employed. The reactants were placed in a 250 ml round bottomed flask equipped as described in Example D, stirring was begun, and the mixture was heated at reflux overnight. Water was removed by a Dean trap, and the alkenyl disulfone was formed.

Example F

Preparation of Reagent F and Analysis by Formation of Compound 7

To prepare PDFMs in which a trimethine group is desired to be introduced between the disulfone group and the ring of an aromatic tertiary amine, the olefinic group of a dye base or dye olefin, or the ring of an activated heterocyclic compound, it is convenient to prepare and use a disulfone-containing reagent containing an active species $CH_3O-CH=CH-CH=C(SO_2CF_3)_2$. Such a material (Reagent F) has been produced, for example, using the following procedure.

In a 125 ml Erlenmeyer flask equipped with air condenser, the following were mixed: 14.00 g (0.05 mole) bis(trifluoromethanesulfonyl)methane; 8.20 g (0.05 mole) 1,1,3,3,-tetramethoxypropane; and 20.4 g (0.20 mole) acetic anhydride. An exothermic reaction occurred which was controlled by means of a water bath. The resultant 42.6 g reaction mixture was "aged" for 24 hours at approximately 25° C. After aging, the reagent became dark amber-brown in color. Alternatively, aging can be accelerated by maintaining the mixture in a closed vessel (to prevent loss of methyl acetate formed as a by-product) at 60° C. for one hour, or at 90° C. for 20 minutes; or one might utilize an open vessel and permit loss of methyl acetate, provided appropriate correction were made in the weight of any aliquot portions used in subsequent reactions.

The quality of Reagent F was tested by placing a 4.26 g (10%) aliquot of the reagent in a stoppered 8 ml vial with 0.61 g of dimethylaniline, and mixing Reagent F and dimethylaniline by vigorous shaking. After at least ten minutes, and optionally after warming to 60° C., the partially-crystallized product was worked up by dilution, filtration, and washing the retained crystalline product (a total of 100 ml of isopropanol was used for this purpose). The dried product, compound 7, weighed approximately 1.71 g (80% yield based on the disulfone reagent) and had a melting point of 207°–209° C.

Variations in the above reaction conditions have not been found to be significantly beneficial to yield and/or purity of the product. Thus, in a variation termed F-1, a freshly-made golden-yellow reagent was "aged" at about 25° C. for two minutes, and the product weighed 0.64 g (30% yield). In other variations termed F-2 and F-3, after aging the reagent at approximately 25° C. for 1 hour and for 4 hours, 61% and 68% yields were obtained respectively. In a variation F-4, a 71% yield was obtained after aging the reagent at 60° C. for 20 minutes. In an equilibrium reaction, an increase above the stoichiometric amount of an equilibrated reagent would be expected to increase the yield. In a variation F-5, a 25% excess of acetic anhydride was added and the yield was 75%. In a variation F-6, a 25% excess of 1,1,3,3,-tetramethoxypropane was added to the reaction mixture, and the yield was 78%. In a variation F-7, in which both reactants were present at 25% excess, the yield was 84%. This improvement is considered to be just outside the limits of error (±2%) of the test method.

Example G

Preparation of Reagent G and Analysis by Formation of Compound 9

When a one-carbon methine is desired for use in preparing PDFMs, it can be made as described in Example F using the following reactants in the following amounts: 7.41 g (0.05 mole) of triethyl orthoformate (CAS 122-51-0); 14.00 g (0.05 mole) of bis(trifluoromethylsulfonyl)methane; and 15.3 g (0.15 mole) of acetic anhydride. After aging at 25° C. for about 24 hours, a 3.67 g aliquot (0.005 equivalents) of Reagent G is reacted in a stoppered 8 ml vial with 1.33 g (0.005 mole) of 1,1-bis(p-dimethylaminophenyl)ethylene (CAS 7478-69-5) 1 hr at 60° C. Reagent G contains the active species $C_2H_5)-CH=C(SO_2CF_3)_2$. The partly-crystalline mixture is diluted with 50 to 100 g of isopropanol, heated on the steam bath to dissolve the crystals, cooled to below room temperature to effect recrystallization, filtered, washed, and dried. At least 2.13 g of compound 9 (78% yield based on the disulfone), is recovered if Reagent G has been properly aged before use.

Example H

Preparation of Reagent H Containing $(C_2C_5O)-CH=C(SO_2CF_3)_2$

Triethylorthoformate (7.41 g, 0.005 mol) and 31 g of acetic anhydride were placed in a 100 ml round-bottomed flask equipped with a condenser and magnetic stirrer. Stirring was begun, and upon the dissolving of the reactants, the solution was cooled in an ice bath, and stirred for 10 minutes. Bis(trifluoromethylsulfonyl)methane (14.03 g, 0.005 mol) was slowly added to minimize the exotherm. The ice bath was replaced with a cold water bath, and the reaction mixture was allowed to slowly warm to room temperature. After 15 minutes, the water bath was removed, replaced with a heating mantle, and the yellow-orange solution was heated at 65° C. for 1 hour. The solution was cooled to room temperature. Each 2.62 g of this solution was calculated to contain 0.0025 mol of the vinyl ether disulfone adduct.

Example J

Preparation of Reagent J Containing $CH_3O-CH=CH-CH=C(SO_2C_8F_{17})_2$ 1,1,3,3-Tetramethoxypropane, 0.18 g (0.0011 mole), 0.51 g (0.005 mole) of acetic anhydride, and 0.98 g (0.001 mole) of $(C_8F_{17}SO_2)_2CH_2$ (CAS 29214-34-4) were placed in a stoppered 8 ml vial and heated on the steam bath to 95°–100° C. for one-half hour. The initially golden-yellow pasty mix became a clear, reddish-amber-brown solution, designated Reagent J.

Example K

Preparation of Reagent K Containing $CH_3O-CH=CH-CH=C(SO_2CF_3)(SO_2C_8F_{17})$

In a stoppered 8 ml vial 0.37 g (0.0022 mole) of 1,1,3,3,-tetramethoxypropane and 0.82 g (0.008 mole) of acetic anhydride was added to 1.26 g (0.002 mole) of $CF_3SO_2CH_2SO_2C_8F_{17}$ (CAS 30416-80-9). The mixture was heated on a steam bath to 90°–100 ° C. for ¾ hour. An amber-brown solution (Reagent K) was formed.

Example L

Preparation of Reagent L Containing CH$_3$O—CH=CH—CH=C(SO$_2$F)$_2$

Reagent L was prepared by the process of Example K, except 0.36 g (0.002 mole) of CH$_2$(SO$_2$F)$_2$, CAS 42148-23-2, was substituted for the CF$_3$SO$_2$CH$_2$SO$_2$C$_8$F$_{17}$. An amber-brown solution of Reagent L was obtained, and remained in solution on cooling to room temperature.

Example 1

Bis(trifluoromethylsulfonyl)methane (3.00 g, 0.011 mol) and acetic anhydride (25 ml) were placed in a 250 ml round-bottomed flask and were stirred magnetically to obtain a solution. The solution was cooled in an ice bath, and a solution of 1.60 g (0.01 mol) 1,1,3,3,-tetramethoxypropane in 25 ml of acetic anhydride was slowly added. Upon completion of the addition, the cooling bath was removed and replaced by a heating mantle. The solution was then heated at 70° C. for 2 hr, was then cooled to room temperature, and a solution of 1.21 g (0.01 tool) of N,N-dimethylaniline (CAS 121-69-7) in 5 ml of acetic anhydride was added dropwise. A heating mantle was attached, and this solution was heated at 70° C. for 2 hours. As the reaction progressed, the solution became deep magenta. The solution was allowed to cool, 125 ml of isopropyl alcohol was added slowly, and the solution was stirred overnight. Filtration, followed by washing with methanol and drying, afforded 2.70 g (62%) of compound 1. Its spectrum in 1,2-dichloroethane (used for all spectra unless otherwise stated) showed maximal absorption λmax at 544 nm, with half-maximal absorption points λ½ at 516 and 565 nm.

Example 2

An acetal reactant was prepared in a manner similar to the reaction described in J. Klein & E. D. Bergmann, *J. Amer. Chem. Soc.* 1957, 79, 3452–54. This was accomplished by adding 1.49 g (0.01 mol) of p-N,N-dimethylamino-benzaldehyde (CAS 100-10-7), 100 ml of toluene, 1.75 g (0.012 mol) of triethyl orthoformate, and a few milligrams of p-toluenesulfonic acid to a 250 ml round-bottomed flask equipped with magnetic stirrer, condenser, heating mantle, and dry nitrogen atmosphere. Stirring and heating were begun, and the solution was heated at reflux overnight to form p-dimethylaminobenzaldehyde bis(diethylacetal).

The solution of Example D containing the alkenyl disulfone CH$_3$—CH=CH—CH=C(SO$_2$CF$_3$)$_2$ was added to the acetal solution, and an immediate green solution resulted. The resultant solution was heated at reflux, and the reaction was monitored by thin-layer chromatography (TLC).

Upon cooling, the reaction mixture was filtered and diluted with an equal amount of hexanes to crystallize the resulting PDFM. Filtration and drying afforded 0.76 g (16%) of compound 2 as green needles. This compound's spectrum had λmax at 634 nm and λ½ at 596 and 666 nm.

Example 3

Bis(trifluoromethylsulfonyl)methane (2.80 g, 0.010 mol) and 35 ml of toluene were placed in a 100 ml round-bottomed flask equipped with magnetic stirrer, condenser, and nitrogen atmosphere. Upon dissolution of the bis(trifluoromethylsulfonyl)methane, a solution of 1.48 g (0.01 mol) of triethyl orthoformate in 5 ml of toluene was added to the round-bottomed flask. Cooling in an ice bath was followed by adding 3.36 g (0.033 mol) of acetic anhydride in 5 ml of toluene. The ice bath was removed and replaced by a heating mantle. The solution was heated at 50°–70° C. for 3 hr, was then cooled in an ice bath, and a solution of 1.49 g (0.010 mol) of N,N-diethylaniline (CAS 91-66-7) in 5 ml of toluene was added dropwise. A heating mantle was attached, and the solution was heated at 50°–70° C. for 3 hr. As the reaction progressed, the solution became deep yellow. The solution was allowed to cool, and 200 ml of isopropyl alcohol was slowly added. Upon further cooling, a fine yellow precipitate separated out from the solution. Filtration, followed by drying, afforded 2.3 g (54%) of compound 3. This compound's spectrum showed λmax at 455 nm and λ½ at 427 and 470 nm.

Example 4

A 2.12 g aliquot of the vinyl ether disulfone solution of Example A, calculated to contain 0.871 g (0.0025 mol) of (CH$_3$O)—CH=CH—CH=C(SO$_2$CF$_3$)$_2$, was placed into a small reaction flask, followed by the addition of 0.37 g (0.0025 mol) of N,N-diethylaniline. A reaction occurred, and the product was isolated by pouring the mixture into a 75/25 (by volume) mixture of methanol and water to precipitate the product, compound 4. This compound's spectrum showed λmax at 549 nm and λ½ at 522 and 569 nm.

Example 5

A 2.12 aliquot of the vinyl ether disulfone solution of Example A, calculated to contain 0.871 g (0.0025 mol) of (CH$_3$O)—CH=CH—CH=C(SO$_2$CF$_3$)$_2$, was placed in a small reaction flask, followed by the addition of 0.44 g (0.0025 mol) of N,N-di-n-propylaniline (CAS 2217-07-4). A reaction occurred, and the product was isolated by pouring the mixture into a 75/25 (by volume) mixture of methanol and water to precipitate the product, compound 5. This compound's spectrum showed λmax at 552 nm and λ½ at 524 and 572 nm.

Example 6

Compound 6 was prepared as described in Example 1, except that the following were used: 7.00 g (0.025 mol) of bis(trifluoromethylsulfonyl)methane; 4.10 g (0.025 mol) of 1,1,3,3,-tetramethoxypropane; 4.06 g (0.025 mol) of N-phenylmorpholine (CAS 92-53-5); and 25 ml of acetic anhydride. Yield was 2.0 g (17%) of compound 6. This compound's spectrum had λmax at 538 nm and λ½ at 504 and 564 nm.

Example 7

Compound 7 was prepared as described in Example 1, except that bis(trifluoromethylsulfonyl)methane, 1,1,3,3,-tetramethoxypropane, julolidine (CAS 479-59-4), and acetic anhydride were used. Compound 7 was formed having λmax at 571 nm and λ½ at 539 and 590 nm.

Example 8

An acetal reactant was prepared by adding 1.36 g (0.01 mol) of p-anisaldehyde (CAS 123-11-5), 100 ml of hexanes, and 1.75 g (0.012 mol) of triethyl orthoformate to a 500 ml round-bottomed flask equipped with magnetic stirrer, condenser, heating mantle, and nitrogen atmosphere. Stirring and heating were begun, and the solution was heated at reflux overnight to form p-anisaldehyde bis(diethylacetal), CAS 2403-58-9.

The solution of Example E containing the alkenyl disulfone $CH_3$—$CH$=$CH$—$CH$=$C(SO_2CF_3)_2$ was cooled and was then poured into the solution containing the acetal reactant. The resulting solution was heated at reflux, the reaction was monitored by TLC, and an orange solid was formed upon cooling. Filtration and drying afforded 1.00 g (22%) of compound 8.

Example 9

Compound 9 was prepared as described in Example 3, except that 2.80 g (0.010 mol) of bis(trifluoromethylsulfonyl)methane, 1.48 g (0.010 mol) of triethyl orthoformate, 2.66 g (0.010 mol) of 1,1-bis-(N,N-dimethylaminophenyl)ethylene, (CAS 7478-69-5) and 3.06 g (0.010 mol) of acetic anhydride were used. The product was recrystallized three times from isopropanol to afford 4.26 g (78%) of compound 9 as dark iridescent green crystals having λmax at 533 nm, and λ½ at 504 and 586 nm.

Example 10

Isolated vinyl ether disulfone of Example B of the formula $(CH_3O)$—$CH$=$CH$—$CH$=$C(SO_2CF_3)_2$ (1.74 g, 0.005 mol) and 40 g of absolute ethanol were placed in a 100 ml round-bottomed flask equipped with magnetic stirrer. A solution of 0.87 g (0.005 mol) of 1,3,3-trimethyl-2-methylene-indoline (also known as "Fischer's Base", CAS 118-12-7) was slowly added to the flask. An immediate dark color developed. Stirring was maintained for 2 hr, after which TLC indicated the presence of a green and a yellow/orange component. Solvent removal at reduced pressure was followed by column chromatography on silica gel and elution with chloroform. The yellow/orange component was eluted first. Recrystallization from methanol/ether/pentane afforded 0.80 g (33%) of compound 10.

Example 11

A 2.12 g aliquot of the reaction product of Example A, calculated to contain 0.871 g (0.0025 mol) of $(CH_3O)$—$CH$=$CH$—$CH$=$C(SO_2CF_3)_2$ was placed in a small reaction flask, followed by the addition of 0.43 g (0.0025 mol) of N,N-dimethyl-1-naphthylamine (CAS 86-56-6). A reaction occurred, and the product was isolated and purified by recrystallization from methanol. Filtration and drying afforded compound 11 as metallic green crystals having λmax at 594 nm, and λ½ at 566 and 613 nm.

Example 12

Chloroform (50 ml), 1.68 g (0.005 mol) of an enamine disulfone, $(CH_3)_2N$—$CH$=$C(SO_2CF_3)_2$, (CAS 58510-91-1) and 2.06 g (0.005 mol) of 1,3-diethyl-2-methylimidazo[4,5b]quinoxalinium tosylate (prepared as described in U.S. Pat. No. 3,431,111) were placed in a 100 ml round-bottomed flask equipped with magnetic stirrer and condenser. Stirring was begun, and upon dissolution of the reactants, 0.51 g (0.005 mol) of triethylamine was added. An immediate orange colored solution resulted. After stirring for 3 hr, TLC still indicated the presence of starting material. An additional equivalent of triethylamine was added. After an additional 3 hours, starting material remained, and the reaction was heated at reflux overnight. Although the reaction was still not complete, the reaction mixture was allowed to cool and was terminated. The solution was washed twice with 100 ml of water and dried over anhydrous magnesium sulfate for several hours. The drying agent was removed by filtration, and solvent was removed at reduced pressure. The product was purified by recrystallization from methanol to afford 1.13 g (43%) of compound 12. This compound's spectrum showed λmax at 433 nm and λ½ at 408 and 444 nm.

Example 13

Bis(trifluoromethylsulfonyl)methane (0.28 g, 0.001 mole), 0.16 g (0.001 mole) of 1,1,3,3,-tetramethoxypropane, 0.41 g (0.004 mole) of acetic anhydride, and 0.27 g (0.001 mole) of 1,1-bis(N,N-dimethylaminophenyl)ethylene were mixed in a stoppered 8 ml vial and shaken. After a few minutes, the mixture solidified to a mass of damp crystals, which were worked up in approximately 10 ml of hot isopropanol. Upon cooling, filtration, and drying, 0.46 g of compound 13 as dark crystals was obtained in 80% of the theoretical yield. The crystals produced blue solutions in organic solvents, and had λmax at 641 nm and λ½ at 604 and 670 nm.

Example 14

The aged Reagent F of Example F (4.26 g, 0.005 mol equivalents) was mixed with 0.96 g (0.005 mole) of N,N-diethyl-m-phenetidine (CAS 1864-92-2) in a stoppered 8 ml vial and rapidly formed a deep magenta product. Workup in approximately 50 ml of methanol:water (3:1 by weight) gave, after filtration and drying, 2.16 g of compound 14 as crystals (86% yield, crude), which after recrystallizing from 100 ml of ethanol:water (3:1 by weight) and drying weighed 1.94 g (77% yield) and had λmax (in 1,2—$C_2H_4Cl_2$) at 537 nm and λ½ at 512 and 555 nm. In dimethylsulfoxide of its molar absorbances were measured to be 21.8 (790 nm), 8.89 (830 nm), and 0.00 (1300 and 1560 nm). In 1,2—$C_2H_4Cl_2$ its electric-field-induced second harmonic (EFISH) generation at 790 nm was 11.0 times that of p-nitroaniline (standard), the irradiation being at 1580 nm.

Example 15

Compound 15 was prepared by the method of Example 14, except 1.61 g (0.005 mole) of 1,1-bis(p-diethylaminophenyl)ethylene (CAS 6961-56-4) was used instead of the phenetidine compound. A deep blue reaction mix was produced. Upon workup in methanol, 2.02 g of compound 15 (64% yield) was formed. This compound formed greenish-blue solutions in organic solvents; in 1,2—$C_2H_4Cl_2$ the λmax was 646 nm, and the λ½ were 609 and 681 nm.

Example 16

Compound 16 was prepared by the method of Example 14, except that 0.90 g (0.005 mole) of 2,5-dimethoxy-N,N-dimethylaniline (CAS 4034-94-1) was used instead of the phenetidine compound. A deep purplish product was formed, which was worked up in isopropanol to form 1.73 g crystals. The crystals were recrystallized using aqueous 60 wt.% acetone to give 1.56 g (64% yield) of compound 16. The crystals produced purplish solutions in organic solvents, and had λmax at 568 nm and λ½ at 526 and 592 nm. Its EFISH generation at 790 nm was 8.2 times that of p-nitroaniline (irradiation at 1580 nm).

Example 17

Compound 17 was prepared by the method of Example 14, except that 0.65 g (0.005 mole) of N-methylindole (CAS 603-76-9) was used instead of the phenetidine compound. A red-amber liquid product was formed, which upon workup in a 3:1 (by weight) methanol:water solution formed 1.89 g of crystals. Recrystallization from aqueous 50 wt.% acetone gave 1.61 g (74% yield) of compound 17 having $\lambda$max at 477 nm and $\lambda\frac{1}{2}$ at 455 and 498 nm.

Example 18

Reagent G of Example G (3.67 g, 0.005 mol equivalents) was mixed with 0.65 g (0.005 mole) of N-methylindole and was heated overnight in a stoppered 8 ml vial on a steam bath. Crystals formed, and the product was worked up by mixing it with 75 g of methanol and 25 g of water. The precipitate was filtered off and dried, giving 1.63 g of compound 18 as a red-brown powder (78% yield). Solutions containing compound 18 were immensely yellow in color. This compound's spectrum showed $\lambda$max at 402 nm and $\lambda\frac{1}{2}$ at 375 and 423 nm.

Examples 19a, b, c (a) 4-Dimethylaminobenzaldehyde, 0.60 g (0.0040 mole) was dissolved in 15 ml of isopropanol, and to the solution was added 1.00 g (0.0034 mole) of $CF_2(CF_2SO_2)_2CH_2$, CAS 126136-11-6. The mixture was stirred under reflux for 3 hours, cooled to room temperature, and allowed to crystallize overnight. The solid product was filtered off, washed with isopropanol, and dried, giving 1.09 g (75% yield) of compound 19a as yellow crystals having $\lambda$max at 450 nm.

(b) The procedure of (a) was repeated except the molar scale was reduced by 15% and $(CF_2SO_2)_2CH_2$ was used in lieu of $CF_2(CF_2SO_2)_2CH_2$. $(CF_2SO_2)_2CH_2$ may be obtained in a manner similar to that described for CAS 126136-11-6. The recovered product 19b had yellow crystals weighing 0.90 g (83% yield) and had $\lambda$max at 453 nm, and $\lambda\frac{1}{2}$ at 427 and 472 nm.

(c) The procedure of (b) was repeated except for increasing the molar scale by a factor of 2.7 and substituting 4-dimethylaminocinnamaldehyde (CAS 6203-18-5) for 4-dimethylaminobenzaldehyde. The dark crystals of product 19c, 2.90 g (93% yield), had a blue reflex, and a $\lambda$max at 537 nm, and $\lambda\frac{1}{2}$ at 505 and 562 nm.

Example 20

One-half of Reagent L (0.001 molar equivalent) was mixed with 0.12 g (0.001 mole) of dimethylaniline. A reaction occurred at once to give a deep red-magenta mixture which was heated at at 90°-100° C. for approximately one-half hour. The partly-solid product was diluted with isopropanol, filtered, and washed with isopropanol until the filtrate was no longer amber-colored. The product was then leached with acetone to extract compound 20 and leave unwanted residues behind. Upon evaporation of acetone from the filtrate, the solid residue, 0.15 g (44% yield) had $\lambda$max at 525 nm and $\lambda\frac{1}{2}$ at 492 and 550 nm. Its molar absorbances in the near-infrared region were measured as: 2.32 (790 nm), 0.39 (830 nm) and 0.00 (1300 and 1580 nm) in dimethylsulfoxide solution. In 1,2-dichloroethane its EFISH generation at 790 nm was 20.9 times that of p-nitroaniline.

Example 21

Dimethylaniline (0.14 g, 0.0011 mole) was added to Reagent J of Example J, and the 8 ml vial was shaken vigorously. A deep magenta color formed. After 15 minutes about 7 ml of isopropanol was added to precipitate the product. After 10 minutes, the mixture was filtered, and the precipitate was washed with three 8 ml portions of isopropanol and dried, giving 0.64 g (56% yield) of compound 21. Compound 21 displayed enough solubility in nonpolar solvents to show solvatochromy. The compound was very slightly soluble in pentane, cyclohexane, and hot perfluoro(ethylcyclohexane) to give pale yellow to yellowish-orange solutions. In a 6:4 perfluoro(ethylcyclohexane): bis(trifluoromethyl)benzene mixture, a light red solution was formed, in bis(trifluoromethyl)benzene a reddish magenta solution was formed, and in warm dimethylsulfoxide a bluish magenta solution was formed. A saturated solution in 1,2-$C_2H_4Cl_2$ had $\lambda$max at 549 nm and $\lambda\frac{1}{2}$ at 520 and 571 nm.

Example 22

The aged Reagent G of Example G (3.67 g, 0.005 equivalents) was reacted with 1.11 g (0.005 mole) of 1-p-anisyl-2,5-dimethylpyrrole (CAS 5044-27-9) to form an amber-yellow solution from which (in about 5 minutes) crystals began to separate. After 2 hours at approximately 40° C., the mix was worked up with 100 ml of 3:1 (by weight) methanol:water. After filtration and drying of the light-yellow product, there was recovered 1.71 g (67% yield) of compound 22. Compound 22 formed pale yellow solutions in organic solvents; its $\lambda$max in 1,2—$C_2H_4Cl_2$ was at 362 nm.

Example 23

Compound 23 was prepared by the method of Example 14, except that 1.11 g (0.005 mole) of 1-p-anisyl-2,5-dimethylpyrrole was used instead of the phenetidine compound. A crystalline product was obtained upon cooling after 2 hours at approximately 50° C. The product was worked up with 100 ml of 3:1 (by weight) methanol:water to give, upon filtration and drying, 2.20 g of compound 23 (82% yield). This compound formed red-orange solutions in organic solvents.

Example 24

Compound 24 was prepared as described in Example 20, except 0.26 g (0.001 mole) of 1,1-bis(p-dimethylaminophenyl)ethylene was used in lieu of dimethylaniline. Compound 24 was isolated in 77% yield and had $\lambda$max at 630 nm and $\lambda\frac{1}{2}$ at 575 and 660 nm. Solutions of it in organic solvents were intensely blue.

Example 25

Chloroform (50 ml), 1.68 g (0.005 mol) of enamine disulfone $(CH_3)_2N—CH=C(SO_2CF_3)_2$, and 1.65 g (0.005 mol) of N-methyl-quinaldinium p-toluenesulfonate (CAS 41626-14-6) were placed in a 100 ml round-bottomed flask equipped with magnetic stirrer and condenser. Stirring was begun and upon dissolution of the reactants, 0.426 g (0.005 mol) of piperdine was added. The solution turned yellow, orange, then orange red, indicating an immediate reaction. After 15 minutes, a precipitate developed. Stirring for an additional hour was followed by cooling in ice, filtration, and drying to afford 2.07 g (92% yield) of compound 25. This compound's spectrum showed $\lambda$max at 436 nm and $\lambda\frac{1}{2}$ at 401 and 453 nm.

Example 26

The steps of Example 25 were repeated, except 1.65 g (0.005 mol) of N-methyl-lepidinium p-toluenesulfonate (CAS 42952-26-1) was used in lieu of N-methyl-quinaldinium p-toluenesulfonate. The solution turned yellow indicating an immediate reaction, and a precipitate developed. Stirring for an additional 1.5 hours was followed by cooling in ice, filtration, and drying to afford 2.05 g (92%) of compound 26.

Example 27

Chloroform (40 ml), 1.68 g (0.005 mol) of enamine disulfone $(CH_3)_2N-CH=C(SO_2CF_3)_2$, and 1.53 g (0.005 mol) of N-ethyl-2-methylbenzothiazolinium iodide (CAS 3119-93-5) were placed in a 100 ml round bottomed flask equipped with magnetic stirrer and condenser. Stirring was begun and upon dissolution of the reactants, 0.426 g (0.005 mol) of piperidine was added. The solution turned orange indicating an immediate reaction. After one-half hour no precipitate had formed. The chloroform solution was transferred to a separatory funnel, washed twice with water (2×25 ml), and dried over anhydrous magnesium sulfate. Filtration, followed by solvent removal at reduced pressure afforded the crude product.

The crude product was purified by dissolving it in about 125 ml of absolute ethanol and boiling the solution down to a volume of about 50 ml. Upon cooling, the product precipitated as crystals. Filtration and drying afforded 1.85 g (79%) of compound 27. This compound's spectrum showed $\lambda$max at 411 nm and $\lambda\frac{1}{2}$ at 382 and 432 nm.

Example 28

Methanol (20 ml), and 1.65 g (0.005 mol) of N-methyl-quinaldinium p-toluenesulfonate were placed in a 100 ml round-bottomed flask equipped with magnetic stirrer and condenser. Stirring was begun, and 1.74 g (0.005 mol) of isolated vinyl ether disulfone of Example C of the formula $(CH_3O)-CH=CH-CH=(SO_2CF_3)_2$, was added. Upon dissolution of the reactants, 0.51 g (0.005 mol) of triethyl amine was added. The solution slowly became orange. A heating bath was attached and the solution heated at reflux for 3 hours at which time TLC indicated almost complete clean reaction. The heating bath was removed and the solution allowed to stir for 60 hours. A precipitate developed, Stirring for an addition 60 hours resulted in formation of a precipitate. Cooling in ice, filtration, and drying afforded 1.14 g (48%) of compound 28. This compound's spectrum showed $\lambda$max at 523 nm and $\lambda\frac{1}{2}$ at 477 and 546 nm.

Example 29

Methanol (20 ml), and 1.74 g (0.005 mol) of isolated vinyl ether disulfone of Example C of the formula $(CH_3O)-CH=CH-CH=C(SO_2CF_3)_2$, were placed in a 100 ml round-bottomed flask equipped with magnetic stirrer and condenser. Stirring was begun and upon dissolution of the reactants, 1.65 g (0.005 mol) of N-methyl-lepidinium p-toluenesulfonate was added. Triethyl amine 0.52 g (0.005 mol) was subsequently added. The original pale yellow solution turned pale green and then slowly darkened and became orange. The solution was stirred overnight, a heating bath was attached, and the solution heated at reflux for 4 hours. The heating bath was removed, and the reaction mixture was allowed to cool. Cooling in ice, filtration, and drying afforded 0.95 g (40%) of compound 29. The mother liquors were returned to the reaction flask, an additional 0.52 g (0.005 tool) of triethyl amine was added and the mixture was heated at reflux for an additional 18 hours. Filtration afforded an additional 0.21 g of product. This compound's spectrum showed $\lambda$max at 560 nm and $\lambda\frac{1}{2}$ at 507 and 589 nm.

Example 30

Absolute ethanol (30 ml), 1.57 g (0.005 mol) of N-ethyl-2-methylbenzothiazolinium iodide and 1.74 g (0.005 mol) of isolated vinyl ether disulfone of Example C of the formula $(CH_3O)-CH=CH-CH=C(SO_2CF_3)_2$ were placed in a 100 ml round bottomed flask equipped with magnetic stirrer and condenser. Stirring was begun and, even though not all of the benzothiazole had dissolved, 0.52 g (0.005 mol) of triethyl amine was added. The solution slowly became orange-yellow, and a precipitate developed as additional benzothiazole iodide dissolved. Filtration and drying, followed by boiling in methanol for 20 minutes, cooling, filtering and drying afforded 2.07 g (84%) of Compound 30. This compound's spectrum showed $\lambda$max at 511 nm and $\lambda\frac{1}{2}$ at 468 and 526 nm.

Examples 31a and b (a) One-half of Reagent K (0.001 molar equivalent) was reacted with 0.14 g (0.0011 mole) of dimethylaniline at 35° C. for one-half hour. To the deep magenta solution ws added 7 g of isopropanol and the solution was allowed to crystallize overnight. The solid product, Compound 31a, was filtered off, washed with four 7 ml portions of isopropanol, and dried; it weighed 0.52 g (66% yield) and had $\lambda$max at 547 nm, and $\lambda\frac{1}{2}$ at 520 and 568

(b) By the same procedure as (a) but with the substitution of 0.26 g (0.001 mole) of 1,1-bis-(p-dimethylaminophenyl)ethylene for the dimethylaniline, of methanol:water (3:1 by weight) for the isopropanol, and optionally of centrifugation for filtration compound 31b was obtained in 45% yield and moderate purity. Compound 31b had $\lambda$max at 645 nm and $\lambda\frac{1}{2}$ at 610 and 673 nm. solutions of it in organic solvents were intensely blue.

Example 32

Provided that an electrophilically-reactive site (commonly para relative to the activating tertiary amine group) remains accessible, polysubstitution of the benzenoid ring is permissible in a starting material for the dye-forming reaction. Using the procedure of Example 14, 0.75 g (0.005 mole) of N,N,3,5-tetramethylaniline (CAS 4913-13-7) and 4.26 g of Reagent F gave Compound 31, 1.54 g (66% yield), having $\lambda$max at 544 nm, and $\lambda\frac{1}{2}$ at 518 and 565 nm. Dilute solutions of it in organic solvents were intensely purplish-magenta in color.

Examples 33a–33j

Following the procedure of Example 32, except that the products were not obtained in crystallinine form; intensely-colored (solution colors in parentheses) reaction products, compounds 33a–33j, were obtained by using 0.005 mole amounts of the following reactants (a)–(j) respectively in lieu of N,N,3,5-tetramethyl-aniline:

(a) N-ethyl-benzo[a]carbazole, CAS 82926-38-3, (violet);

(b) N-ethyl-N-(2-cyanoethyl)aniline, CAS 148-87-8, (red);

(c) N-ethyl-N-(2-cyanoethyl)m-toluidine, CAS 148-69-6, (magenta);

(d) N-methyldiphenylamine, CAS 552-82-9, (magenta);

(e) N,N-dibenzylaniline, CAS 91-73-6, (magenta);

(f) N,N-bis(2-acetoxyethyl)aniline, CAS 19249-34-4, (magenta; λmax=538 nm, $\lambda\frac{1}{2}$=506 and 562 nm);

(g) N-(2-acetoxyethyl)-N-(2-cyanoethyl)aniline, CAS 22031-33-0, (reddish-magenta; λmax=527 nm, $\lambda\frac{1}{2}$=486 and 551 nm);

(h) N,N-bis(2-cyanoethyl)m-toluidine, CAS 18934-20-8, (bluish-red; λmax=520 nm, $\lambda\frac{1}{2}$=480 and 543 nm); and (j) N-phenylpyrrole, CAS 635-90-5, (orange).

The great intensity of the colors resulting from the dissolution (in a few hundred ml of solvent) of a milligram of any of these colored, tarry, dried reaction products attests to the formation in good yield of these as-yet-not-crystallized PDFMs.

Example 34

Toluene (5 ml), 0.30 g (0.001 mole) of 4-(bis-p-tolyl-)aminobenzaldehyde, CAS 42906-19-4, and 0.28 g (0.001 mole) of bis(trifluoromethylsulfonyl)methane were placed in a stoppered 8 ml vial, together with 0.60 g $B_2O_3$, CAS 1303-86-2, to absorb by-product water. After a few minutes, the mixture became a strong reddish-amber color. After one-half hour at approximately 50° C., a sample was withdrawn and examined by visible/ultraviolet spectroscopy in 1,2-dichloroethane. There was a strong peak at 357 nm and a second one at 463 nm, about one-fourth as strong. The former was due to the starting aldehyde and the latter to the product. The reaction mixture was heated to 95°-100° C. for about 50 hours, at which time the second peak had greatly intensified, and the former peak was barely discernible as a weak shoulder demonstrating completeness of reaction. The product remained soluble in the toluene and was recovered by evaporation to dryness followed by washing with heptane to remove by-products and any unreacted starting material After drying at 100°, the product was extracted with methyl tertiary-butylether, and on evaporation of the filtrate to dryness, there was recovered 0.43 g (76% yield) of compound 34, a dark-colored solid having λmax at 463 nm and $\lambda\frac{1}{2}$ at 432 and 513 nm.

Example 35

Toluene (40 ml), 3.35 g (0.01 mol) of enamine disulfone $(CH_3)_2N—CH=C(SO_2CF_3)_2$, and 1.73 g (0.01 mol) of 1,3,3-trimethyl-2-methylene-indoline were placed in a 100 ml round bottomed flask equipped with magnetic stirrer and condenser. Stirring was begun, and the solution heated at reflux for 25 hours. The progress of the reaction was monitored by TLC and proceeded smoothly. Upon cooling, crystals precipitated. One-half of the solvent was removed at reduced pressure and the product redissolved by heating. Upon cooling, crystals again developed. Filtration and drying afforded 3.26 g (70%) of compound 35 having λmax at 406 nm and $\lambda\frac{1}{2}$ at 376 and 432 nm.

PREPARATION OF NONLINEAR OPTICALLY EFFECTIVE LAYERS

Examples 36-50

In each of Examples 36-50, a NLO layer was formed on a substrate from a polymeric composition that contained a PDFM (compounds 1-12, 19c, $(CH_3)_2N—C_6H_6—C_4H_4(SO_2CF_2)_2CF_2$, and $(CH_3)_2N—C_6H_6—C_4H_4(SO_2C_4F_9)_2$, respectively) dispersed in a polymer. The prepared layers were then used to perform second harmonic generation (SHG) of light. In Example 37, electro-optic effects were demonstrated.

Example 36

Compound 1 was dissolved in a polar solvent, and PMMA was added to the solution. The solution was then spin-coated onto two coplanar chromium electrodes on a glass slide separated by a gap of 150 micrometers created by conventional photolithographic means. The solvent was evaporated. The coated slide was then placed on a temperature-controlled copper block equipped with a hole to let light pass through the gap. Electrical contact was made to the chromium electrodes using stainless steel clips. The NLO layer was then heated above $T_g$ of the polymer, and a direct current voltage (800-1500V) was applied to the electrodes to align the molecules noncentrosymmetrically. Laser light was then passed through the NLO layer. The incident laser light had a frequency of 1.58 micrometers and was produced by doubling the frequency of outputted light from a Nd:YAG laser using a KDP crystal, and passing that outputted light through a high pressure $H_2$ Raman cell to obtain the third Stokes-shifted wavelength. The light was focused through the electrode gap by means of a cylindrical lens. From the incident light of 1.58 micrometers, second-harmonic light of 790 nanometers was then detected by using a monochromator and a photo-multiplier tube. The layer of NLO material was then cooled while the poling voltage remained, and the applied field was then removed at room temperature. Noncentrosymmetric alignment of the guest molecules, induced by the poling electric field, was maintained after the poling voltage was removed. This was evidenced by a minor change in the intensity of the second harmonic light.

A measure of $\chi^{(2)}$ of the NLO layer was obtained from the ratio of the SHG signal from the NLO layer relative to the SHG signal from a quartz crystal. The product of the dipole moment $\mu$ and the molecular hyperpolarizability $\beta$ was then deduced as taught in D. S. Chemla and J. Zyss, "Nonlinear Optical Properties of Organic Molecules and Crystals", vols. I & II,, ch II-7 and II-8 Academic Press, N.Y. (1987). The product of $\mu$ and $\beta$ is shown in Table 2.

Example 37

A NLO layer was prepared as described in Example 35, except compound 2 and a copolymer of methylmethacrylate and 2-vinyl-4,4-dimethylazlactone (prepared as described in S. Hellmann et al., J. Poly. Sci. 1984, 22, 1179-86 were used in lieu of compound 1 and PMMA, respectively. Second harmonic light was generated at 790 nm from an incident light of 1.58 micrometers. Noncentrosymmetric alignment of the guest molecules was maintained after the poling voltage was removed. The NLO layer was tested for its $\mu,\beta$ product; that value is shown in Table 2.

The NLO layer containing compound 2 was tested for utility as an electro-optic phase shifter. After the poling process was complete and the poling field was removed at room temperature, the NLO layer was placed in the apparatus of FIG. 2 to observe an electro-optic effect. Polarized light at wavelengths of 632.8 nm was passed through the electrode gap. A modulating voltage was applied to the electrodes to produce a phase shift of the electric field component parallel to the modulating electric field (relative to the component perpendicular to the modulating electric field). The phase-shifted light was passed through a phase compensator and a polarizer onto a photo-diode detector. When the applied voltage was modulated, the NLO layer's electro-optic effect produced corresponding changes in the polarization state of the light passing through the NLO layer.

Examples 38–45, and 47–50

NLO layers were prepared as described in Example 35, except that compounds 3-10, 12, 19c, 4-$(CH_3)_2N$—$C_6H_4$—$(CH)_3C(SO_2CF_2)_2CF_2$ and 4-$(CH_3)_2N$—$C_6H_4$—$(CH)_3C(SO_2C_4F_9)_2$ were used respectively in lieu of compound 1. The NLO layers demonstrated SHG by emitting light having a wavelength of 790 nanometers from incident light of 1.58 micrometers. Noncentrosymmetric alignment of the guest molecules was maintained after the poling voltage was removed. The product of $\mu$ and $\beta$ were determined for each sample; those values are shown below in Table 2.

Example 46

A NLO layer was prepared as described in Example 37, except that compound 11 was used as a guest molecule in lieu of compound 2. The NLO layer demonstrated SHG by emitting light having a wavelength of of 790 nm from incident light of 1.58 micrometers. Noncentrosymmetric alignment of the guest molecules was maintained after the poling voltage was removed. The product of $\mu$ and $\beta$ was determined; that value is shown in Table 2. Under these conditions the standard test compound, p-nitroaniline, gives 1-0 for the product of $\mu$ and $\beta$ (in $10^{28}$ Debye-esu).

TABLE 2

| Example | Compound | $\mu\beta \times 10^{28}$ Debye-esu |
|---|---|---|
| 35 | 1 | 15 |
| 36 | 2 | 37 |
| 37 | 3 | 2.9 |
| 38 | 4 | 12 |
| 39 | 5 | 12 |
| 40 | 6 | 11.5 |
| 41 | 7 | 7.0 |
| 42 | 8 | 9.8 |
| 43 | 9 | 11.7 |
| 44 | 10 | 7.6 |
| 45 | 11 | 4.6 |
| 46 | 12 | 1.2 |
| 47 | 19c | 17.7 |
| 48 | *4-$(CH_3)_2N$—$C_6H_4$—$(CH)_3C(SO_2CF_2)_2CF_2$ | 8.4 |
| 49 | **4-$(CH_3)_2N$—$C_6H_4$—$(CH)_3C(SO_2C_4F_9)_2$ | 7.0 |

The product of the $\mu$ and $\beta$ values demonstrates that PDFMs possess a relatively large dipole moment and hyperpolarizability.
*This compound may be prepared as described in Example 19a by using 4-dimethylaminocinnamaldehyde in lieu of 4-dimethylaminobenzaldehyde.
**This compound may be prepared as described in Example 21 by using $(C_4F_9SO_2)_2CH_2$ (CAS 29214-37-7) in lieu of $(C_8F_{17}SO_2)_2CH_2$.

Examples 51–62

In Examples 51, 56, 59, and 61, the light absorption characteristics for PDFMs were examined over the molecule's highest-wavelength peak. In Comparative Examples 52–55, 57–58, 60, and 62, the light absorption characteristics for polar-functionalized molecules having electron-accepting groups other than a disulfone group (yet with similar donor groups) were examined over the same band of wavelengths. The tests were performed by dissolving the molecules in dichloroethane at $10^{-5}$ molar concentrations, and measuring the molecules' light absorption characteristics in a spectrometer.

The molecules tested and the results of the absorption measurements are shown in Table 3. The "half-height-half-bandwidth" $\Delta v_{\frac{1}{2}}$ is equal to the number of wave numbers away from peak absorption and at longer wavelength, where the absorption is $\frac{1}{2}$ the peak value. $\Delta v_{1/10}$ represents the analogous point at 1/10 of peak absorption.

TABLE 3

| Example | Structure | $\Delta v_{1/2}$ ($\times 10^3$ cm$^{-1}$) | $\Delta v_{1/10}$ ($\times 10^3$ cm$^{-1}$) |
|---|---|---|---|
| 51. | $H_3C$-N($H_3C$)-C$_6$H$_4$-CH=CH-CH=C(SO$_2$CF$_3$)(SO$_2$CF$_3$) | 0.70 | 1.22 |
| 52. | $H_3C$-N($H_3C$)-C$_6$H$_4$-CH=CH-CH=C(CN)(CN) | 1.46 | 2.37 |
| 53. | $H_3C$-N($H_3C$)-C$_6$H$_4$-CH=CH-C$_6$H$_4$-NO$_2$ | 2.22 | 3.69 |
| 54. | $H_3C$-N($H_3C$)-C$_6$H$_4$-CH=CH-CH=C(COOC$_2$H$_5$)(COOC$_2$H$_5$) | 1.94 | 3.35 |

TABLE 3-continued

| Example | Structure | Δν₁/₂ (× 10³ cm⁻¹) | Δν₁/₁₀ (× 10³ cm⁻¹) |
|---|---|---|---|
| 55. | H₃C\N-C₆H₄-CH=CH-CH=C(CN)(COOC₂H₅), H₃C/ | 1.83 | 2.87 |
| 56. | H₃C\N-C₆H₄-CH=C(SO₂CF₃)₂, H₃C/ | 0.73 | 1.41 |
| 57. | H₃C\N-C₆H₄-CH=C(CN)(COOC₂H₅), H₃C/ | 1.09 | 1.86 |
| 58. | H₃C\N-C₆H₄-CH=C(CN)₂, H₃C/ | 1.01 | 1.70 |
| 59. | H₃CO-C₆H₄-CH=CH-CH=C(SO₂CF₃)₂ | 1.20 | 1.98 |
| 60. | H₃CO-C₆H₄-CH=CH-CH=C(CN)₂ | 1.92 | 3.08 |
| 61.* | H₃CO-C₆H₄-CH=C(SO₂CF₃)₂ | 1.14 | 1.98 |
| 62. | H₃CO-C₆H₄-CH=C(CN)₂ | 1.74 | 2.60 |

*Compound 61 was made from p-anisaldehyde (CAS 123-11-5) by the method of U.S. Pat. No. 3,933,914.

The data shown in Table 3 demonstrate that the PDFMs absorb less light at long wavelengths when compared to polar molecules having similar electron-donating groups. The PDFMs are shown to have a narrower absorption peak, absorbing less light in and near the infrared region. This is deemed to be a very important property for NLO materials intended to operate with diode lasers as the light source.

Example 63

Attaching a PDFM to a Polymer

In this example, a polymer was prepared which had a polar moiety comprising a disulfone-functionalized group covalently bonded to the polymer's sidechains. The prepared polymer (a) had the following structure:

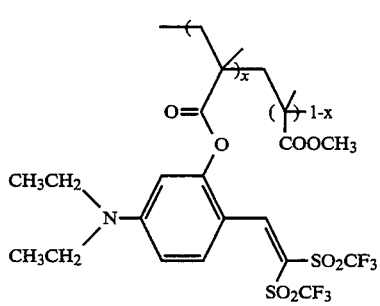

where x is as defined above. To prepare this polymer, poly(methacryloyl chloride) (0.21 g, 2 mmol equivalents, from Polyscience, Inc., Warrington, Pa.) and 1,1-bis(trifluoromethanesulfonyl)-2-(2-hydroxy-4-(N,N-diethylamino)phenyl)ethane:

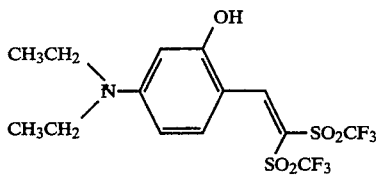

(0.91 g, 2 mmol prepared as described in U.S. Pat. No. 3,933,914, Example 1 by using 2-hydroxy-4-(N,N-diethylamino) benzaldehyde (CAS 17554-90-4) instead of p-dimethylaminocinnamaldehyde) were dissolved in 20 ml of anhydrous 1,2-dichloroethane and warmed to 70° C. under dry nitrogen with stirring. Anhydrous pyridine (0.32 g, 4 mmol) was added all at once with a syringe. The reaction proceeded exothermically. After 4 hours of additional heating, the reaction was cooled, and the product precipitated by adding 200 ml methanol. The product was collected by filtration, and after vacuum drying weighed 0.09 g. TLC showed no free PDFMs present. Using absorption measurements, it was determined that x was approximately 0.03.

Preparation and measurement techniques were identical to those used for the PDFMs dispersed in PMMA. The polymer was spin coated onto a pair of co-planar chromium electrodes on a fused silica substrate and was poled at 145° C. with a field of $6 \times 10^4$ volts/cm. The polymer successfully generated second harmonic light at 790 nm from irradiation by light having a fundamental wavelength of 1580 nm. The signal level was consistent with measurements made on Compound 3 (Example 3) dispersed in PMMA. That is, at the same concentration of NLO groups and film thickness, essentially the same signal level was observed relative to the SHG signal from a quartz crystal. After poling, the film was cooled to room temperature while maintaining the field. The second harmonic signal showed virtually no change after the field was removed, indicating stable alignment of the polar moiety in the polymer.

Various modifications and alterations of this invention will become apparent to those skilled in the art without departing from the scope and spirit of this invention. It therefore should be understood that the scope of this invention is not to be limited to illustrative embodiments set forth herein, but is to be determined by the limitations set forth in the claims and equivalents thereof. It is to be further understood that this invention may be suitably practiced in the absence of any element that is not disclosed herein.

What is claimed is:

1. A nonlinear optical composition of matter, which comprises: polar disulfone-functionalized molecules incorporated in and aligned noncentrosymmetrically in an optically clear polymeric composition, wherein the polar disulfone-functionalized molecules are of the Formula I

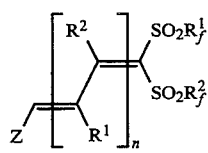

where n is 0, 1, or 2; $R^1$ and $R^2$ each independently represent hydrogen, an alkyl group of about 1 to 4 carbon atoms, or taken together in conjunction with the catenary carbon atoms therebetween form a 5 or 6-membered carbocyclic or heterocyclic ting, when n is 2, $R^1$ and $R^2$, $R^1$ and $R^1$, or $R^2$ and $R^2$, in conjunction with the catenary carbon atoms therebetween, may form the 5 or 6-membered carbocyclic or heterocyclic ring; $R_f^1$ and $R_f^2$ each independently represent fluorine, a saturated fluorinated alkyl radical having 1 to 10 carbon atoms, or taken together in conjunction with the disulfone group form a 5, 6, or 7-membered ring containing 2, 3, or 4 carbon atoms, respectively, that are fluorinated; and Z represents an aryl group substituted with an electron donating group, an activated aromatic heterocyclic group, a group derived from a dye base, or a group derived from a dye olefin, wherein;

the aryl group substituted with an electron-donating group is represented by the Formula II

where Ar- represents a monovalent aryl group having 6 to 10 ring atoms; Y represents an electron-donating substituent group having up to 20 atoms; X represents a monovalent substituent group having 1 to 20 atoms; k is 1 or 2; and m is an integer of 0 to 6;

the activated heterocyclic aromatic group is represented by the Formula III

where represents a monovalent heterocyclic aromatic nucleus containing 5 or 6 ring atoms: V represents X, or taken together with atoms in the heterocyclic aromatic nucleus represents the necessary atoms required to complete a 6-membered aromatic nucleus; E is S, O, or $NR^5$, where $R^5$ represents a substituent containing up to 20 carbon atoms; and g is an integer of 0 to 4;

the group derived from a dye base is represented by the Formula IV

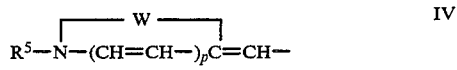

where p is 0, or 1; $R^5$ is as defined above; and W represents the non-metallic atoms required to complete a heterocyclic nucleus containing 5 or 6 atoms in the heterocyclic ring; and the group derived from the dye olefin is represented by the Formula V

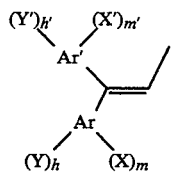

where Ar, Y, X, and m are as defined above; Ar' independently represents Ar; X' and Y' independently represent X and Y, respectively; m' independently represents m; and h and h' independently represents 0, 1, or 2, with the proviso that both h and h' cannot be 0.

2. The nonlinear optical composition of claim 1, wherein the electron-donating group has a $\sigma_p$ value of less than $-0.3$.

3. The nonlinear optical composition of claim 1, wherein the polar disulfone-functionalized molecules are incorporated in the optically clear polymeric composition by chemically reacting the polar disulfone-functionalized molecules with a polymer or with precursors to a polymeric composition.

4. The nonlinear optical composition of claim 1, wherein the carbon atoms of $R_f^1$ and $R_f^2$ adjacent and next adjacent to the —$SO_2$— groups are perfluorinated.

5. The nonlinear optical composition of claim 1, wherein $R_f^1$ and $R_f^2$ are perfluorinated.

6. The nonlinear optical composition of claim 1, wherein $R_f^1$ and $R_f^2$ are both $CF_3$.

7. The nonlinear optical composition of claim 1, wherein

Y and Y' are conjugatively located relative to the conjugating group extending between the electron-donating and electron-withdrawing groups and independently are an amino group of the formula $R^3R^4N$— or an ether or thio group of the formula $R^3O$— or $R^3S$—, where $R^3$ and $R^4$ independently represent a monovalent alkyl of 1 to 12 carbon atoms, cyanoaklyl of 1 to 4 carbon atoms, an aryl, alkaryl, or arylene group having 6 to 10 ring atoms and less than about 15 total carbon atoms, an alkylene, alkyleneoxy, alkylene-tert-amino, or alkylenethio group 1 to 3 carbon atoms, an alkyleneacylamino having 1 to 3 ring atoms, an aralkyl group of up to about 15 total carbon atoms, or $R^3$ and $R^4$ taken together in conjunction with the nitrogen atom form one or more 5 or 6-membered heterocyclic rings;

E is $NR^5$, where $R^5$ represents a substituent containing up to twenty carbon atoms; and X and X' independently are a halo, a substituted or unsubstituted aryl group Ar- as defined above, a lower alkyl or a substituted lower alkyl having from 1 to 4 carbon atoms, an alkoxy group having from 1 to 4 carbon atoms, a haloalkyl having from 1 to 4 carbon atoms, an acyloxy group having from 1 to 4 carbon atoms, an acylamido having from 1 to 10 carbon atoms, saturated cyclics or heterocyclics having from 3 to 10 carbon atoms, an alkylthio group having from 1 to 10 carbon atoms, an aryl or substituted aryl group having 6 to 10 ring atoms, an aralkyl group having from 7 to 15 carbon atoms, an alkenyl having 2 to 15 carbon atoms, or an aralkenyl having from 8 to 15 carbon atoms.

* * * * *

UNITED STATES PATENT AND TRADEMARK OFFICE
CERTIFICATE OF CORRECTION

PATENT NO. : 5,360,582
DATED : November 1, 1994
INVENTOR(S) : Gary T. Boyd et al.

It is certified that error appears in the above-indentified patent and that said Letters Patent is hereby corrected as shown below:

Col. 1, line 48, delete "when the".

Col. 1, line 49, before "optically-responsive", insert --when the--.

Col. 2, line 31, delete the comma after "$R^5$" and insert --is--.

Col. 4, line 28, after "chemical" insert --group--.

Col. 6, line 20, "buryfoxy" should be --butyroxy--.

Col. 6, line 63, delete formula III and replace with the following formula

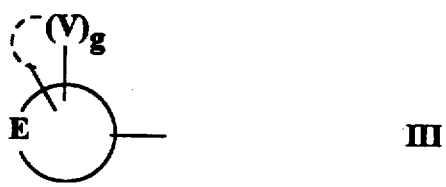   III

Col. 7, line 4, delete formula and before "represents" insert 

Col. 10, line 2, "-napthylenecarbonyli," should be ---napthylenecarbonyl),--.

Col. 11, line 57, after "depending" insert --on,--.

Col. 15, line 3, "$\chi X^{(2)}$" should be --$\chi^{(2)}$--.

UNITED STATES PATENT AND TRADEMARK OFFICE
CERTIFICATE OF CORRECTION

PATENT NO. : 5,360,582
DATED : November 1, 1994
INVENTOR(S) : Gary T. Boyd et al.

It is certified that error appears in the above-indentified patent and that said Letters Patent is hereby corrected as shown below:

Cols. 15 & 16, delete chemical reaction (ib) and replace with the following:

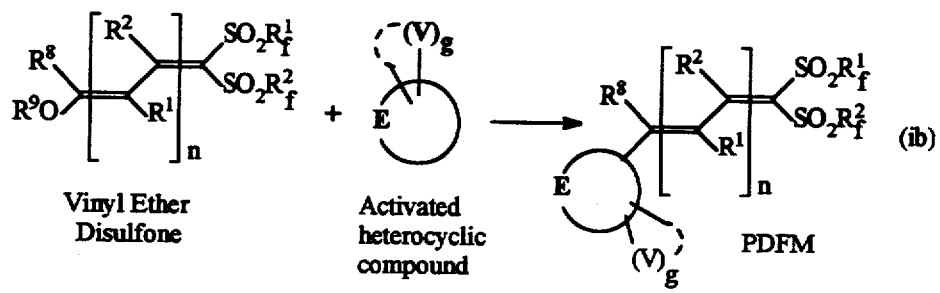

Cols. 17 & 18, in chemical reaction (ic), delete the "Vinyl Ether Disulfone" structure and replace with the following:

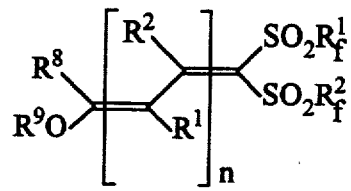

UNITED STATES PATENT AND TRADEMARK OFFICE
CERTIFICATE OF CORRECTION

PATENT NO. : 5,360,582
DATED : November 1, 1994
INVENTOR(S) : Gary T. Boyd et al.

Page 3 of 4

It is certified that error appears in the above-indentified patent and that said Letters Patent is hereby corrected as shown below:

Cols. 17 & 18, delete chemical reaction (id) and replace with the following:

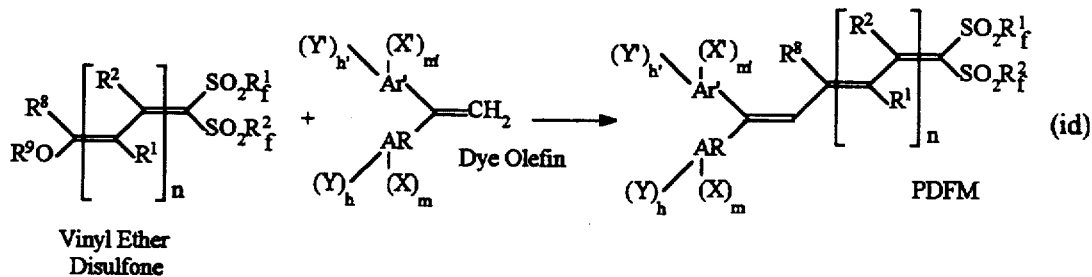

Cols. 19 & 20, structure "(iv)" should be --(iiib)--.

Col. 21, line 64, "CH-CH=C($SO_2CF_3$)($SO_2C_8F_{16}$) should be -- CH-CH=C($SO_2CF_3$)($SO_2C_8F_{17}$)--.

Col. 23, line 35, between "and" and "are" insert --Z--.

Col. 39, line 5, after "Dean" insert --Stark--.

Col. 45, line 22, delete "immensely" and replace with --intensely--.

Col. 47, line 48, delete the comma after "developed" and insert a period.

Col. 48, line 3, "tool" should be --mol--.

UNITED STATES PATENT AND TRADEMARK OFFICE
CERTIFICATE OF CORRECTION

PATENT NO. : 5,360,582
DATED : November 1, 1994
INVENTOR(S) : Gary T. Boyd et al.

It is certified that error appears in the above-indentified patent and that said Letters Patent is hereby corrected as shown below:

Col. 48, line 36, after "568" insert --nm.--.

Col. 48, line 44, before "solutions" insert --Dilute--.

Col. 56, line 1, "ting" should be --ring--.

Col. 56, line 33, delete formula III and replace with the following:

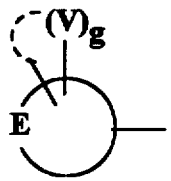

Col. 56, line 44, delete "E -" and replace with the following:

Signed and Sealed this

Second Day of May, 1995

Attest:

BRUCE LEHMAN

Attesting Officer                Commissioner of Patents and Trademarks